(12) United States Patent
Getgey et al.

(10) Patent No.: US 7,311,108 B2
(45) Date of Patent: *Dec. 25, 2007

(54) MOTORIZED FLOSSER AND METHOD OF USE

(75) Inventors: William F. Getgey, Cincinnati, OH (US); Lewis Ray Dyson, Milford, OH (US); Carl R. Andry, Lawrenceburg, IN (US); Gregory R. Furnish, Louisville, KY (US)

(73) Assignee: The William Getgey Company, Inc., Cincinnati, OH (US)

( * ) Notice: Subject to any disclaimer, the term of this patent is extended or adjusted under 35 U.S.C. 154(b) by 13 days.

This patent is subject to a terminal disclaimer.

(21) Appl. No.: 11/224,896

(22) Filed: Sep. 13, 2005

(65) Prior Publication Data

US 2006/0054180 A1 Mar. 16, 2006

Related U.S. Application Data

(63) Continuation-in-part of application No. 10/682,443, filed on Oct. 9, 2003.

(51) Int. Cl.
*A61C 15/00* (2006.01)
(52) U.S. Cl. ..................................................... 132/322
(58) Field of Classification Search ........ 132/321–329; 433/118, 112; 15/22.1, 22.2, 22.4, 28, 29
See application file for complete search history.

(56) References Cited

U.S. PATENT DOCUMENTS

| 1,640,607 | A |   | 8/1927 | Kitley |
| 2,372,731 | A |   | 4/1945 | Nalbach et al. |
| 2,754,833 | A |   | 7/1956 | Vecchio |
| 2,807,820 | A |   | 10/1957 | Dinhofer |
| 3,156,936 | A |   | 11/1964 | Hartmen et al. |
| 3,160,902 | A |   | 12/1964 | Aymar |
| 3,178,754 | A |   | 4/1965 | Cleverdon |
| 3,240,077 | A |   | 3/1966 | Smith |
| 3,378,017 | A |   | 4/1968 | Stiles |
| 3,978,852 | A |   | 9/1976 | Annoni |
| 4,156,620 | A |   | 5/1979 | Clemens |
| 4,245,658 | A | * | 1/1981 | Lecouturier ................. 132/322 |

(Continued)

OTHER PUBLICATIONS

Gregg A. DuPong, DVM, *Understanding dental plaque: biofilm dynamics*, Journal of Veterinary Dentistry, vol. 14, No. 3, Sep. 1997.

(Continued)

*Primary Examiner*—Robyn Doan
(74) *Attorney, Agent, or Firm*—Wood, Herron & Evans, LLP

(57) ABSTRACT

A motorized flosser comprising an elongated body and a flossing head secured to an end portion of the elongated body. The flossing head oscillates in an arcuate manner. A battery powered motor drives a drive mechanism which reciprocates an output drive shaft, which drive shaft is in turn connected through a flexible drive rod to a drive disc. The drive disc oscillates in a rotary arcuate motion to impart either pure rotary arcuate oscillatory motion or a combined rotary arcuate motion and translatory motion to flossing material carried by a yoke of the flossing head. The flossing head may incorporate a toothpaste holder mounted upon the flossing head or toothbrush bristles mounted upon tines of the yoke of the flossing head.

47 Claims, 17 Drawing Sheets

U.S. PATENT DOCUMENTS

| | | | |
|---|---|---|---|
| 4,292,705 A | 10/1981 | Stouffer | |
| 4,445,858 A | 5/1984 | Johnson | |
| D299,560 S | 1/1989 | Dalton | |
| 4,807,752 A | 2/1989 | Chodorow | |
| 5,033,150 A * | 7/1991 | Gross et al. | 15/22.1 |
| 5,127,415 A | 7/1992 | Preciutti | |
| 5,170,809 A | 12/1992 | Imai | |
| 5,183,064 A | 2/1993 | Barth | |
| 5,184,632 A | 2/1993 | Gross et al. | |
| 5,261,430 A | 11/1993 | Mochel | |
| 5,267,579 A | 12/1993 | Bushberger | |
| 5,279,314 A | 1/1994 | Poulos et al. | |
| 5,331,983 A | 7/1994 | Father | |
| 5,348,473 A | 9/1994 | Kivlighan, Jr. | |
| 5,353,460 A | 10/1994 | Bauman | |
| 5,359,747 A | 11/1994 | Amakasu | |
| 5,411,041 A | 5/1995 | Ritter | |
| 5,461,744 A | 10/1995 | Merbach | |
| 5,564,446 A | 10/1996 | Wiltshire | |
| 5,571,012 A | 11/1996 | Witherby et al. | |
| 5,573,020 A | 11/1996 | Robinson | |
| 5,579,786 A | 12/1996 | Wolk et al. | |
| 5,617,601 A * | 4/1997 | McDougall | 15/22.1 |
| 5,650,035 A | 7/1997 | McGaha et al. | |
| 5,662,130 A | 9/1997 | Wiltshire | |
| 5,666,983 A | 9/1997 | McCullough et al. | |
| RE35,712 E | 1/1998 | Murayama | |
| 5,709,233 A | 1/1998 | Boland et al. | |
| 5,738,124 A | 4/1998 | Cervato | |
| 5,762,078 A | 6/1998 | Zebuhr | |
| 5,769,102 A | 6/1998 | Zebuhr | |
| 5,799,674 A | 9/1998 | Ali et al. | |
| 5,896,867 A | 4/1999 | McGaha et al. | |
| 5,921,254 A | 7/1999 | Carlucci et al. | |
| 6,000,083 A | 12/1999 | Blaustein et al. | |
| 6,047,711 A | 4/2000 | Wagner | |
| D424,748 S | 5/2000 | Dolan | |
| 6,138,689 A | 10/2000 | Stern | |
| 6,178,579 B1 | 1/2001 | Blaustein et al. | |
| 6,189,693 B1 | 2/2001 | Blaustein et al. | |
| 6,360,395 B2 | 3/2002 | Blaustein et al. | |
| 6,371,294 B1 | 4/2002 | Blaustein et al. | |
| 6,564,940 B2 | 5/2003 | Blaustein et al. | |
| D494,712 S | 8/2004 | Getgey | |
| 6,836,917 B2 | 1/2005 | Blaustein et al. | |
| 6,886,570 B2 | 5/2005 | Lai et al. | |
| 6,932,216 B2 | 8/2005 | Blaustein et al. | |
| 2002/0178519 A1 | 12/2002 | Zarlengo | |
| 2004/0035439 A1 | 2/2004 | Lai et al. | |
| 2004/0079384 A1 | 4/2004 | Lai et al. | |
| 2004/0187887 A1 | 9/2004 | Beckman | |
| 2004/0194797 A1 | 10/2004 | Xin | |
| 2005/0000537 A1 | 1/2005 | Junkins | |

OTHER PUBLICATIONS

Casey Chen, PhD, DDS and Sandra K. Rich, RDH, MPH, PhD, *Biofilm Basics*, Dimensions of Dental Hygiene, Feb./Mar. 2003.

B. Guggenheiim, E. Giertsen, P. Schupbach, and S. Shapiro, *Validation of an* in vitro *Biofilm Model of Supragingival Plaque*, Journal of Dental Research, 80(1) 2001.

Justin Merrit; Maxwell H. Anderson, DDS, MS, MEd; No-Hee Parks, DDS, PhD; and Wenyuan Shi, PhD, *Bacterial Biofilm and Dentistry*, CDA Journal, vol. 29, No. 5, May 2001.

S.R. Wood, J. Kirkham, P.D. Marsh, R.C. Shore, B. Nattress, and C. Robinson, *Architecture of Intact Natural Human Plaque Biofilms Studied by Confocal Laser Scanning Microscopy*, Journal of Dental Research, 79(1) 2000.

Pamela R. Overman, RDH, MS, *Biofilm: A New View of Plaque*, The Journal of Contemporary Dental Practice, vol. 1, No. 3, Summer Issue, 2000.

Casey Chen, DDS, PhD, *Periodontitis as a Biofilm Infection*, CDA Journal, Vo. 20, No. 5, May 2001.

Caren M. Barnes, RDH, MS, *The Bottom Line*, Dimensions of Dental Care, Feb./Mar. 2003.

\* cited by examiner

MOTORIZED FLOSSER AND METHOD OF USE

This application is a Continuation-in-Part application of U.S. application Ser. No. 10/682,443, filed Oct. 9, 2003 and entitled "Motorized Flosser and Associated Method of Use".

FIELD OF THE INVENTION

The present invention relates to dental hygiene and more particularly to a power driven instrument for flossing teeth.

BACKGROUND OF THE INVENTION

The importance of practicing proper dental hygiene has been well documented. In this regard, it is extremely advantageous to frequently and systematically remove plaque and debris from around and between an individual's teeth. Failure to religiously remove debris and plaque from between and around teeth is likely to lead to dental disease including tooth decay, gingivitis and the like.

Conventional flossing often requires one to put his or her hands in his or her mouth. This may lead to illness due to the increased potential of the spread of bacteria. Another drawback with conventional flossing is that the used dental floss must be properly discarded in a trash receptacle or other appropriate location. Due to the flexible nature of used dental floss it is often difficult to discard the used piece of dental floss in the location the user wishes to discard it. The conventional manual method of flossing one's teeth is cumbersome due to the difficulty in maneuvering a piece of dental floss to the desired position in one's mouth. Individuals with small mouths have a particularly difficult time of flossing using the manual method. Another difficulty with conventional flossing is that it is difficult to fit the floss between teeth which are tightly squeezed together. It often requires a great deal of time, force and effort to properly locate the piece of dental floss for it to fit between two adjacent teeth. Another drawback with conventional flossing is that the gingival sulcus, the area on the gum line between teeth, commonly does not get cleaned or rubbed free of debris.

Therefore, there is a need for a flossing apparatus which is easy to use while keeping one's hands out of one's mouth, which is able to more easily fit a piece of floss between adjacent tight teeth, and which is able to clean the gingival sulcus.

Motorized toothbrushes are known. The commercial market has seen the introduction of many different types of motorized toothbrushes over the last several years. The tendency in the technology is towards more complex, expensive and non-commercially feasible methods of achieving motorized motions in the bristles and heads of toothbrushes. Related U.S. Pat. Nos. 6,000,083; 6,178,579; 6,189,693 and 6,360,395 disclose motorized toothbrushes in which batteries in the handle of the toothbrush power a motor in the handle to oscillate or rotate an elongated shaft which is so connected as to effect a circular motion of bristles in the toothbrush head. Each of these U.S. patents is fully incorporated by reference herein. The oscillation of the elongated shaft causes oscillation of a circular portion of the head to which a plurality of bristles are attached.

Motorized flossing devices are also known. For example, U.S. Pat. No. 5,411,041 discloses a motorized flosser for removing debris from between teeth and around teeth. The motorized flosser has a flossing implement detachably connected to the main body of the instrument. The flossing implement has a pair of tines between which extends a piece of floss. When activated, a motor reciprocates an output shaft which causes the flossing instrument to reciprocate. One drawback to such apparatus is that this straight reciprocal movement of the piece of dental floss does not adequately clean debris such as food particles from teeth. The piece or length of floss does not sweep across the teeth but instead only rubs against a very small area of the teeth.

It is further well known to convert a power driven toothbrush into a power driven flossing device by changing the heads on the end of a battery powered hand held instrument. For example, U.S. Pat. No. 5,762,078 discloses a detachable flosser head for a motorized toothbrush. A drive shaft in the handle assembly reciprocates causing the flosser head to reciprocate. Again, this straight reciprocal movement of the piece of dental floss does not adequately clean debris such as food particles from teeth.

U.S. Pat. No. 6,047,711 discloses another power driven toothbrush which may be converted to a power driven flossing device.

Another inherent drawback with known motorized flossers is that they do not adequately remove biofilm from the surface of teeth. Biofilm is a well organized community of cooperating microorganisms. One commonly known biofilm which forms on tooth surfaces is called plaque. Biofilms may be easily destroyed simply by wiping them with a brush or other mechanically abrasive material, disrupting attachment to their substrate.

Therefore, there is a need for a powered flossing apparatus which adequately removes biofilm from the surface of teeth, promotes regular flossing and is easy to use.

SUMMARY OF THE INVENTION

The present invention comprises a motorized flosser having an elongated body having opposed first and second or top and bottom ends. In one embodiment, a replaceable flosser head is removably secured to the first end of the body with a locking mechanism and, in another embodiment, a replaceable floss carrier is removably mounted and secured to the yoke of a flosser head. A power supply is located in a hollow portion of the elongated body. The power supply energizes the flosser head when a user moves a switch located on the exterior of the body. Activation of the power supply causes a drive mechanism to oscillate the flosser head in a pure arcuate motion or, alternatively, in a combined arcuate oscillating and translatory motion. The frequency of oscillation is preferably 2,800 cycles per minute, but may be any other desired frequency. This rotary oscillation of the flosser head causes a length of flossing material to rotate in an oscillatory manner through an arc and in a preferred embodiment, simultaneously translate in a back and forth motion, as well as move arcuately in an oscillatory motion. This arc of the oscillatory motion generally is between 30 and 90 degrees and preferably is between 45 and 60 degrees.

The elongated body has a lower motorized handle portion having a longitudinal axis extending therethrough and an upper stem portion including the flosser head, the upper stem portion being removable from the lower handle portion. The upper neck portion includes a neck section having a longitudinal axis and an end section to which the flosser head is secured. The power supply includes a motor and batteries within the handle portion of the elongated body. The motor is operably connected or coupled to the flosser head for oscillating or oscillating and translating a flexible length or piece of flossing material extending between two spaced tines on the yoke of the flosser head.

The lower handle portion of the body includes a simplified gear assembly. The gear assembly includes a pinion gear driven by the output shaft of the motor and a crown gear operatively coupled to the pinion gear. The output shaft of the motor rotates the pinion gear which rotates the crown gear. A link assembly is operatively coupled to the gear assembly in the interior of the handle portion of the body and is operative to convert rotation of the crown gear into linear reciprocation of an output link contained in the handle portion of the body. This output link is in turn connected through an appropriate linkage contained in the stem portion of the body to affect oscillatory motion of the flossing head.

In one embodiment of the invention, the reciprocable output link contained in the lower handle portion of the body is connected through a single elongated flexible drive rod contained in the stem portion of the body to an offset of a flossing head drive disc such that this flexible drive rod alone converts linear reciprocating motion of a link in the handle portion of the body into arcuate oscillating motion of the floss-containing yoke of the flossing head. This flexible driving connection to the flossing head is operable to absorb any shock if the flossing head encounters or comes into abrupt contact with a fixed surface as well as prevents potential injury to a tooth or gums resulting from such contact.

The lower handle portion of the body further includes a switch to allow operation of the unit. The switch includes an actuator button and a metal contact. The switch is manually depressed by pressing a molded actuator button down and/or sliding it forwardly, from an "off" position to an "on" position. A metal contact plate is secured to the molded actuator button and once moved forward to the "on" position contacts the motor housing, completing the circuit, as in a conventional momentary switch. The motorized flosser then continuously operates until the button is slid back into an off position toward the rear end of the body and the metal contact of the switch disengages the metal motor housing, thereby interrupting the circuit.

A flexible resilient bite pad in one modification of the flosser is secured to the rear side of head end of the upper stem portion of the body. The bite pad allows a user to comfortably bite down on the head end portion of the motorized flosser to more effectively force the length of flossing material between adjacent teeth.

In one embodiment, the flosser head is removable and replaceable on the head end of the stem portion of the flosser body. In this embodiment, the replaceable flosser head has a base removably and drivably connected to a drive disc contained in the head end of the elongated stem portion of the body. In another embodiment of the present invention, the base of the flosser head is fixedly mounted on the head end of the stem portion of the flosser body and a floss carrier is so mounted in the yoke of the flossing head so as to be removable and replaceable. The floss carrier in this latter embodiment has anchors or caps molded onto opposite ends of a short strip of flossing material, which anchors or caps may be snap-fit into or onto the tines of the yoke so as to facilitate replacement of the floss material.

This invention also envisions that whenever replaceable floss carriers rather than replaceable flossing heads are used in the practice of this invention, that the floss carriers may be used in combination with a floss carrier cartridge to facilitate sanitary removal and replacement of the floss carriers from and onto the tines of the yoke of a flossing head. This floss carrier is so constructed that it holds multiple floss carriers which are so held that a new carrier may be snap-fit in the ends of the tines or onto the tops of the tines by simply pressing the tines down over the anchors or caps on the ends of a floss carrier in the cartridge. And an extractor device is provided on the end of the cartridge and as a part of the cartridge so as to facilitate removal of a used strip of flossing material from the motorized flosser. In the use of this extractor, the floss carrier carrying tines of the yoke of the flosser head are inserted into the extractor and then maneuvered so as to extract the used floss carrier from the tines and leave it in the extractor, all without a user's hand touching or contacting the used floss or floss carrier.

In another embodiment of the present invention, the flosser head further comprises a flexible toothpaste holder, generally in a truncated conical shape and located between the tines of the yoke. This toothpaste holder may or may not contain baffles to enhance this cleaning action of the toothpaste contained in the cup-shaped holder. Other configurations of toothpaste holders may also be used and incorporated into the flosser head if desired. The present invention also may be used without a toothpaste holder if desired.

In yet another embodiment of the present invention, the flosser head includes toothbrush bristles which extend inwardly from the tines of the yoke of the flossing head. Additionally, upwardly extending bristles may be mounted on the base of the flossing head between the tines. These bristles, in use of the flossing head and when coated with toothpaste, enable the flosser to simultaneously floss the teeth and brush them.

In one embodiment of the flossing head, the tines of the yoke of the flossing head extend upwardly from the base of the flosser head and are located in a second plane which intersects a first plane defined by the base of the flosser head at an angle of other than 90 degrees and preferably at about 77 degrees. In another embodiment of the flossing head, the tines are spacially offset from the axis of oscillation of the flossing head. This offset placement and location of the ends of the tines of the flosser head causes the length of flossing material extending between the tines to be offset from the axis of oscillation of the flosser head so as to result in the length of flossing material being caused to translate back and forth in a burnishing or polishing action across a tooth in addition to arcuately oscillating, thereby resulting in a better cleaning action on the surface of the teeth. This back and forth burnishing or polishing action is very similar to the back and forth polishing action encountered when polishing shoes with a shoe shine rag.

In use, once the motorized flosser of the present invention is activated via the switch, the motor, gear assembly and linkage assembly cause a drive disc to oscillate in an arcuate or rotary manner and thereby oscillate the flossing head. A user then presses the oscillatory length of flossing material between two teeth while the flossing head continues to arcuately oscillate, and in some embodiments, translate back and forth. The rotary oscillation of the flossing head makes it easier to fit the length of flossing material between teeth even if the teeth are close together or tightly fit. Once the length of flossing material is located between the teeth, the oscillation of the flossing head causes the length of flossing material to wrap around a front part of a first tooth and a rear part of a second tooth and then about the rear part of the first tooth and front part of the second tooth during each oscillation cycle. Preferably, while the length of oscillatory flossing material is being moved vertically between adjacent teeth, the flossing material is repeatedly and gently pressed toward and away from one of the adjacent teeth so as to cause better cleaning and coverage of the teeth surfaces than has heretofore been possible. And this better cleaning is still further enhanced when the rotary oscillatory motion is further complimented by simultaneous back and forth translatory motion of the flossing material.

If desired, one may insert toothpaste into the toothpaste holder secured to the flosser head or onto bristles attached to the flosser head prior to activating the motorized flosser; such that the teeth are cleaned by the toothpaste and the flossing material while simultaneously being flossed of plaque and biofilm by the oscillating flossing material.

One advantage of the present invention is that the rotary oscillating motion of the flossing head causes a length of flossing material to more easily fit between tight teeth.

Another advantage of the present invention is that toothpaste may be used to help ease the insertion of the flossing material between tight teeth.

Another advantage of the present invention is that the flosser head or alternatively, the floss material carrier, may be quickly and easily replaced and the used flossing material discarded.

Still another advantage of the present invention is that both the front and back of adjacent teeth may be thoroughly cleaned and flossed of plaque and biofilm due to the arcuate oscillating motion or the combined oscillating and translation motion of the flossing head.

These and other objects and advantages of this invention will more readily be apparent from the following description of the drawings.

DETAILED DESCRIPTION OF THE INVENTION

Figure 1:
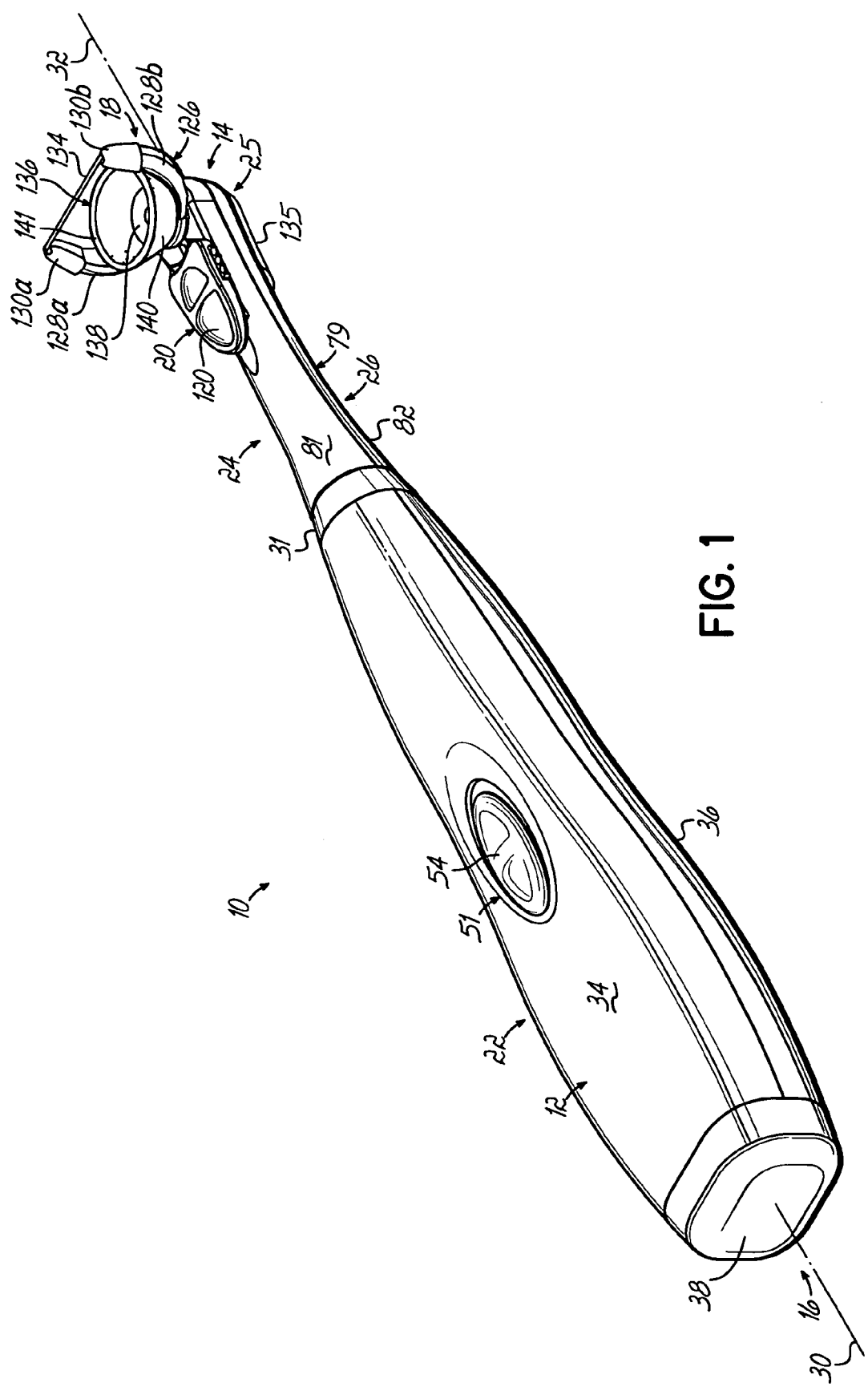
FIG. 1 is a perspective view of a motorized flosser of the present invention.

Referring to the drawings and particularly to FIG. 1, there is illustrated a motorized flosser 10 which encourages and simplifies flossing. The motorized flosser 10 comprises an elongated body 12 having a first or upper end 14 and a second or lower end 16 and a removable/replaceable disposable flossing head 18 which is removably secured to the upper end 14 of the body 12 with a locking mechanism 20. Although one configuration of body 12 is illustrated and described, the motorized flosser 10 may be used with many different configurations or styles of bodies.

As best illustrated in FIG. 1, the body 12 comprises a lower handle portion 22 and an upper stem portion or stem 24 removable from the handle portion 22. The upper stem portion 24 comprises a head end portion 25 and an intermediate or neck section 26 extending between the lower handle portion 22 and the upper head end portion 25. All of the portions or sections 22, 24, 25 and/or 26 may have a hollow interior. The handle portion 22 of the body is removably connected to the neck portion 26 of the stem 24 via engagement of a connector 28 (shown in FIG. 2) secured to the handle portion 22 with at least one projection (not shown) on the inner surface 29 of collar 31 secured to the front portion 24 of the body 12. See FIG. 2. The connector 28 is adapted to mate with and lock together with the collar 31 secured to the stem 24 of the body 12. The stem portion 24 of the body may be removed from the handle portion 22 by a user by grasping the stem 24 and twisting while pulling, as is known in the art. However, the handle portion 22 may be integral with the stem 24, if desired. As best illustrated in FIG. 1, the handle portion 22 has a longitudinal axis 30 and similarly, the neck portion 26 of the stem 24 has a longitudinal axis 32. The longitudinal axes 30 and 32 are preferably co-linear but may be offset if desired. In accordance with the present invention, any other means of coupling the handle portion 22 and stem portion 24 of the body may be used.

Figure 2:
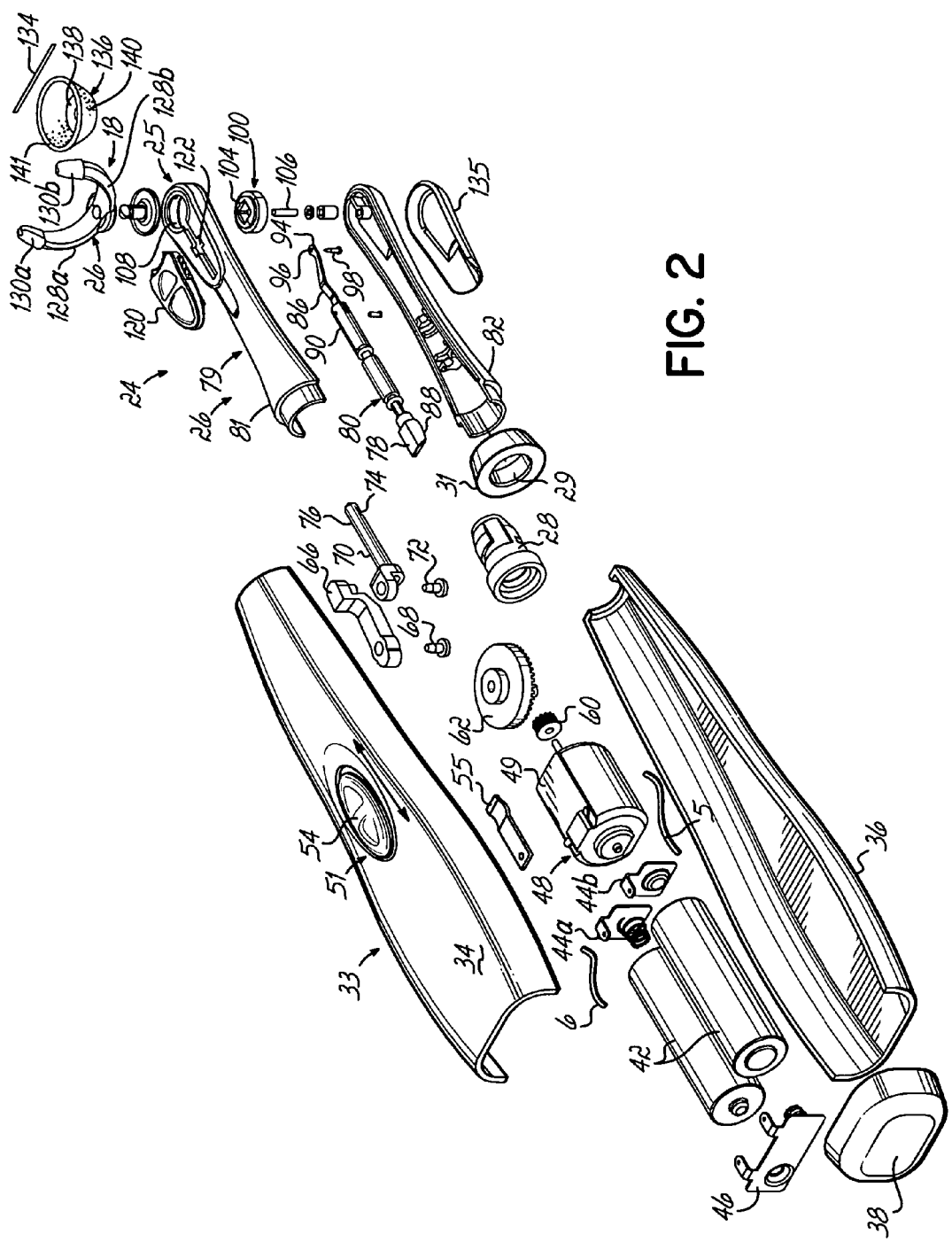
FIG. 2 is a disassembled view of the motorized flosser of FIG. 1.
Figure 3:
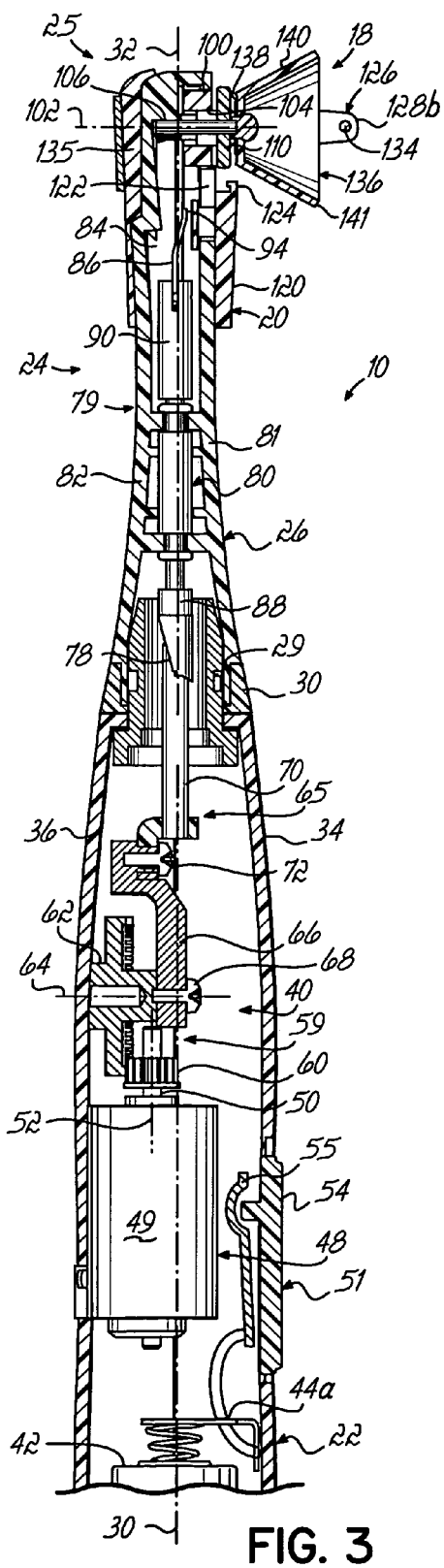
FIG. 3 is a side elevational view in cross section of the motorized flosser of FIG. 1.
Figure 4:
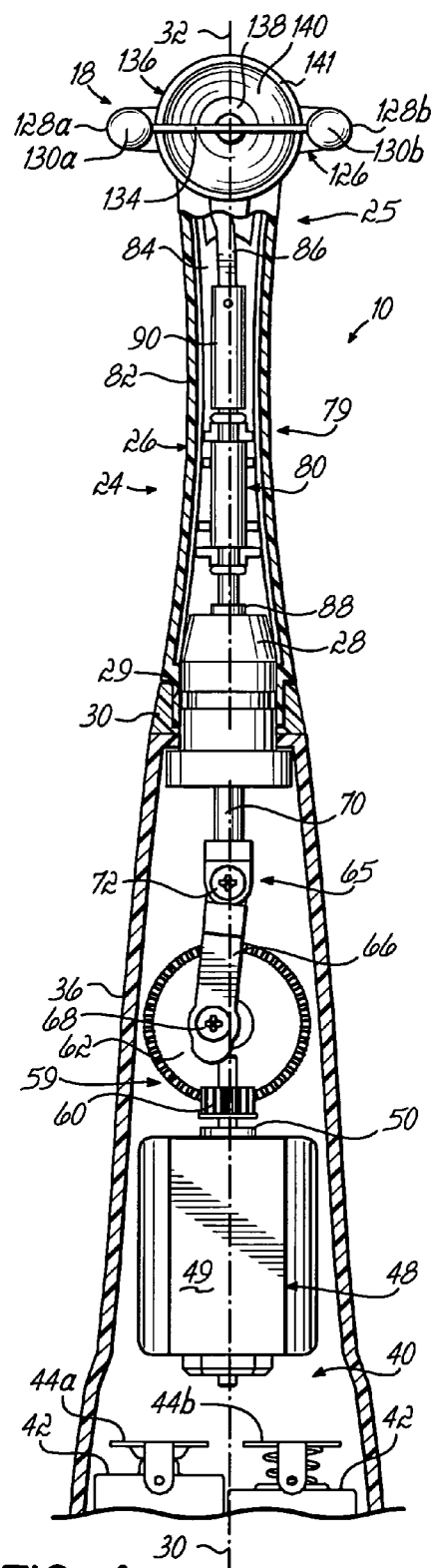
FIG. 4 is a front elevational view in partial cross section of the motorized flosser of FIG. 1.

As best illustrated in FIG. 2, the handle portion 22 of the body comprises a housing 33 having a front housing piece 34, a rear housing piece 36, and a cap or battery door 38 which together with the connector 28, define a hollow interior 40 of the handle portion 22 of the body (see FIGS. 3 and 4). Although one configuration of handle portion 22 is illustrated and described, other configurations of handle portion may be utilized without departing from the present invention. For example, the handle portion may comprise additional pieces at different locations.

As seen in FIGS. 2, 3 and 4, inside the hollow interior 40 of the handle portion 22 of the body is a pair of batteries 42 which are mounted between front battery terminals or contacts 44a, 44b and a common rear battery terminal or contact 46 in a known manner. The front battery terminals or contacts 44a, 44b are secured to one of the housing pieces 34, 36 of the handle portion 22 and the rear battery terminal or contact 46 is secured to the cap 38. The batteries are preferably size AA batteries, but may be any size batteries or single battery. Similarly, any other device may be used to secure at least one battery in place. To install new batteries, the battery door or cap 38 is squeezed or depressed and slid off the end of the handle portion 22. The new battery or batteries is/are then inserted and then the cap 38 is snapped back into place. The terminal ends of the batteries are then in contact with the front and rear battery terminals or contacts.

The hollow interior 40 of the handle portion 22 of the body 12 also houses a motor 48 mounted in a fixed location as shown. The motor 48 has a housing 49 and an output shaft 50 which rotates about an axis 52 when the motor 48 is activated.

As best illustrated in FIG. 2, the motor 48 is activated by the user manually moving a switch 51 including a molded button 54 and a metallic contact plate 55 secured together forwardly from an "off" position to an "on" position. When the switch 51 is in its forward "on" position, the contact plate 55 of the switch 51 presses against or contacts the metal motor housing 49 thereby completing a circuit formed by wire 5 extending between battery contact 44b and the motor housing 49 and wire 6 extending between battery contact 44a and the metallic contact plate 55. The motorized flosser 10 then operates until the switch 51 is moved rearwardly into its "off" position towards the first end of the body 12 and the metallic contact plate 55 disengages from the motor housing 49.

As best seen in FIGS. 3 and 4, rotation of the output shaft 50 of the motor 48 is operatively coupled to a gear assembly 59 including a pinion gear 60 and a crown gear 62. The pinion gear 60 is attached to the output shaft 50 of the motor 48 and is engaged with the crown gear 62. Rotation of the output shaft 50 of the motor 48 causes the pinion gear 60 to rotate about axis 52. See FIG. 3. Rotation of the pinion gear 60 causes the crown gear 62 to rotate about an axis 64 which is generally perpendicular to the axis 52 about which the pinion gear 60 rotates.

A link assembly 65 is operatively coupled or connected to the gear assembly 59. The link assembly 65 includes a first link 66 and a second link 70. The first link 66 is secured to the crown gear 62 with a fastener 68 and is offset from the axis 64 such that rotation of the crown gear 62 causes a linear oscillatory motion of the first link 66. The second link 70 is secured to link 66 with fastener 72. Link 70 passes through the connector 28 as best shown in FIGS. 3 and 4. As best illustrated in FIG. 2, second link 70 has a catch 74 at a forward end 76 thereof. The catch 74 is adapted to engage a receptacle 78 in drive member 80 when the front portion 24 of the body 12 is secured to the handle portion 22 of the body 12. This engagement of the drive member 80 located in the front portion 24 of the body 12 with the link assembly 65 of the handle portion 22 of the body 12 imparts a linear reciprocating movement from the link assembly 65 to the drive member 80, which in turns oscillates the flosser head 18 in a rotary or arcuate manner as described below.

The stem portion or stem 24 of the body 12 comprises a housing 79 having a front housing piece 81 and a rear housing piece 82 which are coupled together to define a hollow interior 84 in which is located the drive member 80 and a link 86. The drive member 80 has a first end 88 towards which the receptacle 78 is located and a second end 90. The link 86 is secured to the drive member 80 and extends upwardly from the drive member 80. The link 86 is non-linear and curved to one side. The link 86 has an upper end 94 which has a hole 96 therein through which passes a pin 98. The pin 98 secures the link 86 to a drive disc 100 which oscillates in an arcuate or rotary manner about a vertical axis 102 due to the offset position of the pin 98 relative to the axis 102 upon reciprocation of the drive member 80.

The oscillating drive disc 100 has a receptacle 104 in the center thereof which is adapted to receive a portion of the flossing head 18 in a manner described below. Although the receptacle 104 is square in shape, it may be other configurations, if desired. A guide pin 106 is secured to the lower housing piece 82 and extends upwardly therefrom. The guide pin 106 functions to properly locate the flossing head. As best illustrated in FIG. 2, the front housing piece 81 of the neck section of the stem 24 has an opening 108 therein through which the guide pin 106 extends. The guide pin 106 extends upwardly from the lower housing piece 82 of the neck through the receptacle 104 in the drive disc 100 and through the opening 108 in the upper housing piece 80 of the neck section of the stem 24. The guide pin 106 is operatively connected or coupled to the flossing head 18 in a manner described below.

Figure 7:
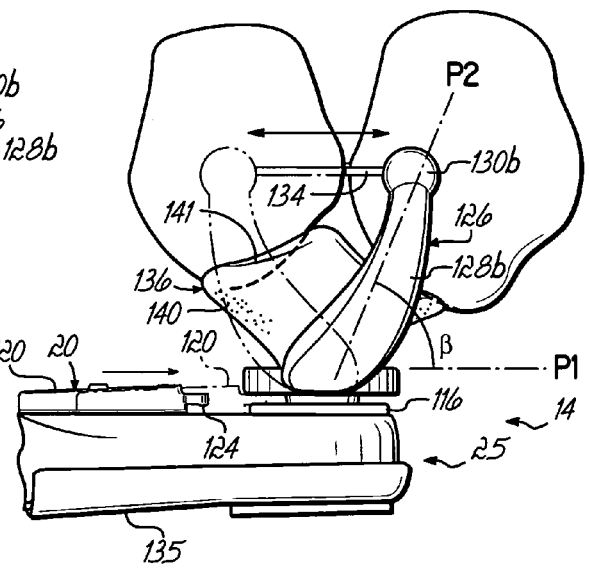
FIG. 7 is a side elevational view of the flossing head of FIG. 5 unlocked from the motorized flosser body and located in the second position of FIG. 6B.
Figure 8:
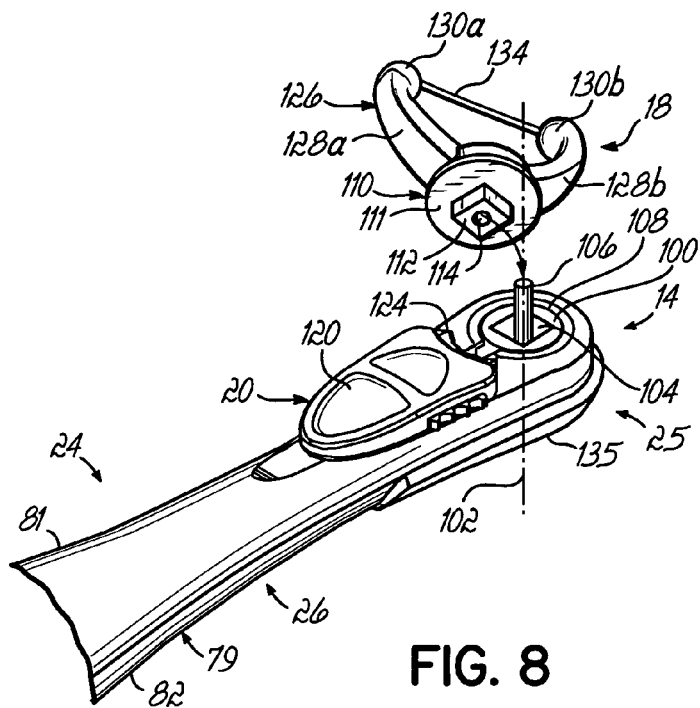
FIG. 8 is an exploded perspective view illustrating how the flossing head is secured to the body of the motorized flosser.

As best illustrated in FIG. 8, the flossing head 18 comprises a base 110 including a circular disc 111 and a projection 112 having a square cross sectional configuration. The projection 112 is adapted to fit snugly or tightly in the receptacle 104 of the drive disc 100. This projection 112 has a guide 114 therethrough which receives the guide pin 106. This mating/coupling between the guide pin 106 and guide 114 of the base 110 of the flossing head 18 and between the projection 112 of the base 110 of the flossing head 18 and the receptacle 104 in the drive disc 100 ensures that the flossing head 18 is correctly seated when the locking mechanism 20 is used to lock the flossing head 18 in a locked position. As shown in FIG. 7, the circular disc 111 of the base 110 of the flossing head 18 has an upwardly extending rim 116 around the periphery of the disc 111.

The locking mechanism 20 is used to lock the flossing head 18 in a locked position in which the motorized flosser 10 may be used and to unlock the flossing head 18 so that it may be separated from the body 12 of the motorized flosser 10 and replaced. The locking mechanism 20 includes a slidable locking member 120 which slides in a slot 122 in the end portion 24 of the body 12 of the flosser 10 and more particularly in the upper housing piece 81 of the neck housing 79. The locking member 120 has a locking lip 124 along the forward edge of the locking member 120, as best shown in FIGS. 3 and 7. The locking member 120 slides between a forward position (shown in dashed lines in FIG. 7) in which the locking lip 124 engages the rim 116 of the circular disc 111 of the base 110 of the flossing head 18 and a rear position (shown in solid lines in FIG. 7) in which the locking lip 124 is behind the circular disc 111 of the base 110 of the flossing head 18. When in its forward, locking position, the locking member 120 prevents the flossing head 18 from being removed or separated from the elongated body 12 of the motorized flosser 10. When in its rear, unlocking position, the locking member 120 allows the flossing head 18 to be removed or separated from the elongated body 12 of the motorized flosser 10. Although one configuration of locking mechanism 20 is illustrated and described, other configurations of locking mechanisms may be utilized to secure the flossing head 18 to the body 22 of the motorized flosser 10 without departing from the present invention.

Figure 5:
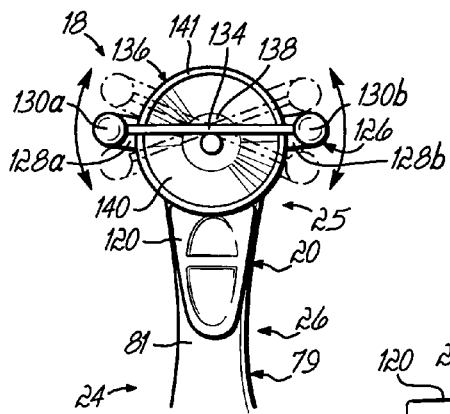
FIG. 5 is a front elevational view of a modified flossing head on the motorized flosser of FIG. 1.
Figure 6A:
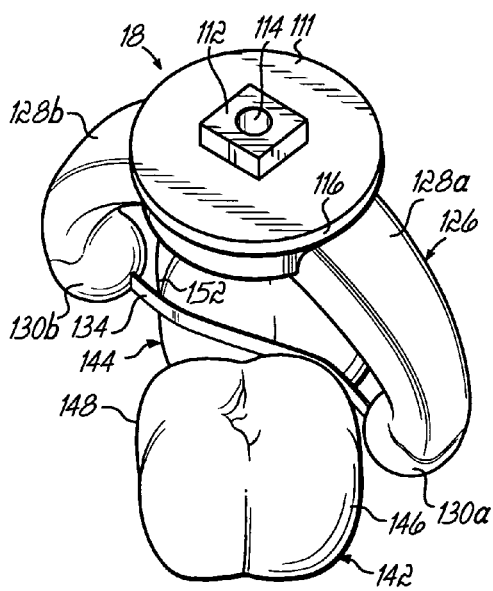
FIG. 6A is an enlarged perspective view of the flossing head of FIG. 5 located in a first end position.
Figure 6B:
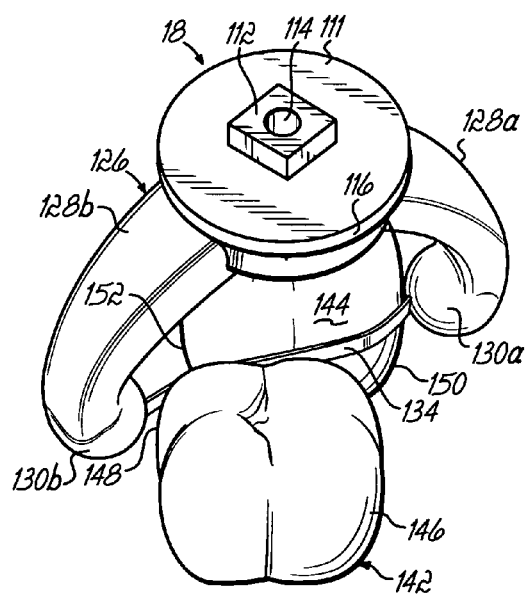
FIG. 6B is an enlarged perspective view of the flossing head of FIG. 5 located in a second end position.
Figure 9A:
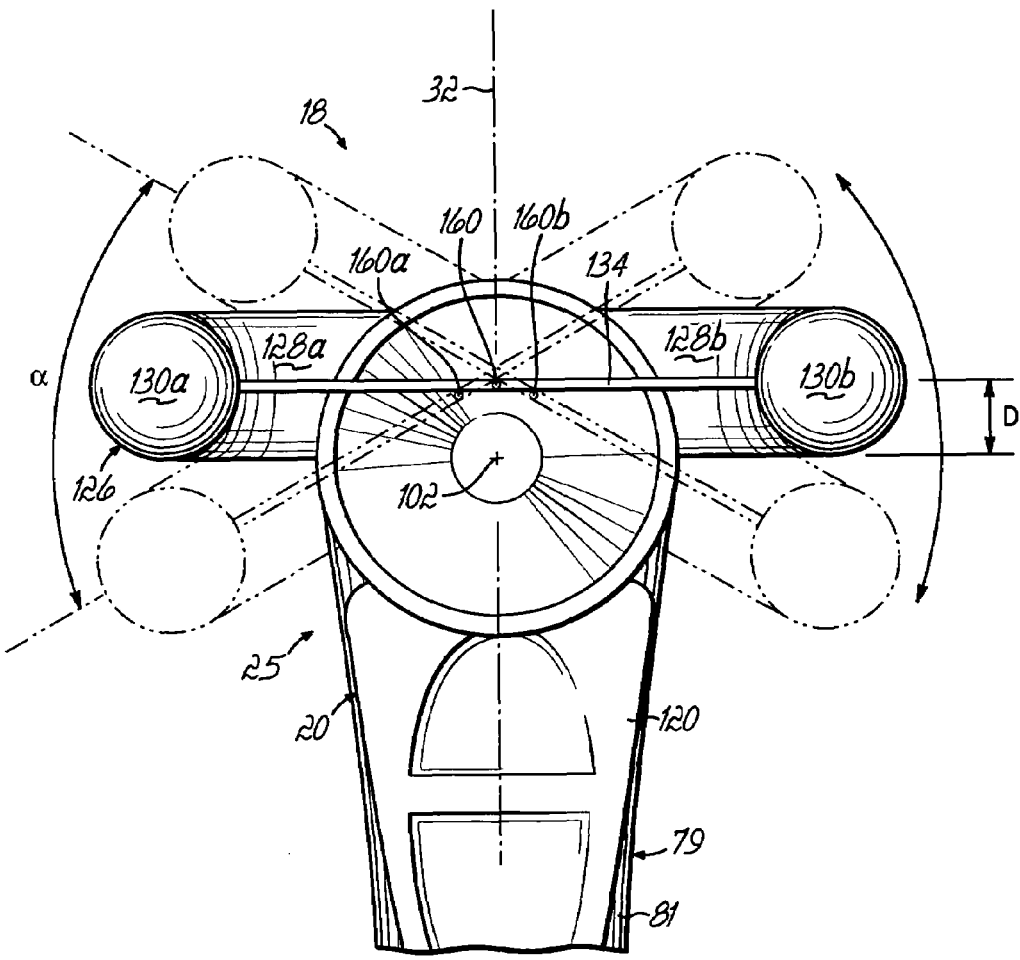
FIG. 9A is an enlarged front elevational view of a portion of FIG. 5 illustrating the translatory as well as the oscillatory motion of the flossing material contained in the flossing head of FIG. 5.
Figure 9B:
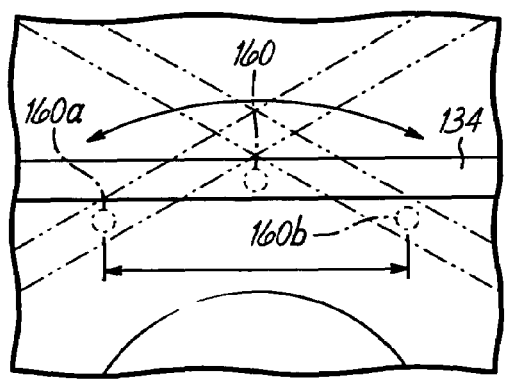
FIG. 9B is an enlarged view of a portion of FIG. 9A.

As best illustrated in FIGS. 6A and 6B, the flossing head 18 further comprises a yoke 126 having a pair of spaced tines 128a, 128b extending upwardly from the base and terminating in end portions 130a, 130b, respectively. Each of the end portions 130a, 130b has a hole (not shown) therein through which passes a length of flexible flossing material 134. The ends of the length of flossing material 134 are tied or otherwise secured to the tines 128a, 128b in any known manner. In one embodiment, the ends of the flossing material are molded into the outer end portions 130a, 130b of the tines. As shown in the embodiment illustrated in FIGS. 5 through 8, the tines 128a, 128b are slightly curved to one side so that the length of flossing material 134 does not pass through the axis 102 about which the flosser head 18 oscillates in an arcuate manner. As shown in FIG. 5, and more clearly emphasized in FIGS. 9A and 9B, the flosser head 18 and, more particularly, the tines 128a and 128b generally oscillate back and forth in an arc of between 30 and 75 degrees. In one preferred embodiment, the tines preferably oscillate back and forth in an arc of 45 degrees. The offset location of the tines 128a, 128b enables the length of flossing material 134 to translate back and forth across the teeth as well as oscillate in the manner shown in FIGS. 6A and 6B. As best illustrated in FIG. 7, the tines of the flosser head define a second plane P2 which intersects with the first plane P1 at an angle β other than 90 degrees and preferably at about 77 degrees. Although one configuration of tine is illustrated and described, the tines of the flosser head may assume other shapes or configurations or even location so long as the ends of the tines and the length of flossing material extending therebetween is offset from an axis of rotation of the flossing head as illustrated in FIGS. 5 and 9A and 9B. Preferably the tines of the flossing head have a coating (most clearly seen in FIG. 12A) of food grade latex or polyurethane or other flexible plastic material to soften any impact of the tines with teeth of a user of the flosser in the event of any such inadvertent contact with the teeth.

With reference now to FIGS. 9A and 9B, there is illustrated in FIG. 9A an enlarged portion of FIG. 5 better illustrating and emphasizing the distance D of the offset of the tines from the axis of rotation 102 of the flossing head 18. When the flossing head 18 and yoke 126 are in their centered position as illustrated in solid lines in FIGS. 5 and 9A, this offset distance D is the same distance as that from the center 160 of the flossing material 134 to the axis of rotation 102 of the flossing head 18. When the flossing head 18 is oscillated about the axis 102 and through an angle α of approximately 45 degrees (22 degrees in each direction from a centered position), the center point 160 of the flossing material translates back and forth between two points 160a and 160b, which translatory distance may be calculated as a function of the offset D. To calculate this translatory back and forth translatory distance or "to and fro" motion, the formula is: total distance of motion equals offset D times the angle of rotation times 2×Pi divided by 360 or 78.4 percent of offset at 45 degrees. For example, if this offset D is 1/10 of an inch, and the flossing head oscillates through an angular arc of 45 degrees, then this translatory movement of a point on the flossing material as, for example, point 160 on the flossing material 134 will be moved or translated back and forth a total distance of approximately 0.00784 inches. Consequently, as the flossing material moves between the teeth vertically while being oscillated about the axis 102 during flossing action of the flossing material, that same flossing material 134 is simultaneously moved back and forth or translated in a burnishing or polishing type motion (similar to a shoe shine motion) because of the offset distance D between the flossing material and its axis of rotation about which it is oscillated.

As shown in FIGS. 6A and 6B, in use, the length of flossing material 134 is pressed between two adjacent teeth, the first tooth 142 and the second tooth 144. The length of flossing material 134 wraps around and contacts the front portion 146 of the first tooth 142 and the rear portion 152 of the second tooth 144 when the flossing head 18 is in a first end position illustrated in FIG. 6A. Similarly, The length of flossing material 134 wraps around and contacts the front portion 150 of the second tooth 144 and the rear portion 148 of the first tooth 142 when the flossing head 18 is in a second end position illustrated in FIG. 6B. This wrapping of the flossing material about the teeth is enhanced and accommodated by the flexing of the tines of the yoke between which the flossing material extends. This flossing action may be further enhanced by the user of the flosser slightly pressing or pulling the floss against a tooth surface while the flossing head continues to oscillate so as to better cover and floss a greater area of a tooth or adjacent teeth.

Figure 6D:
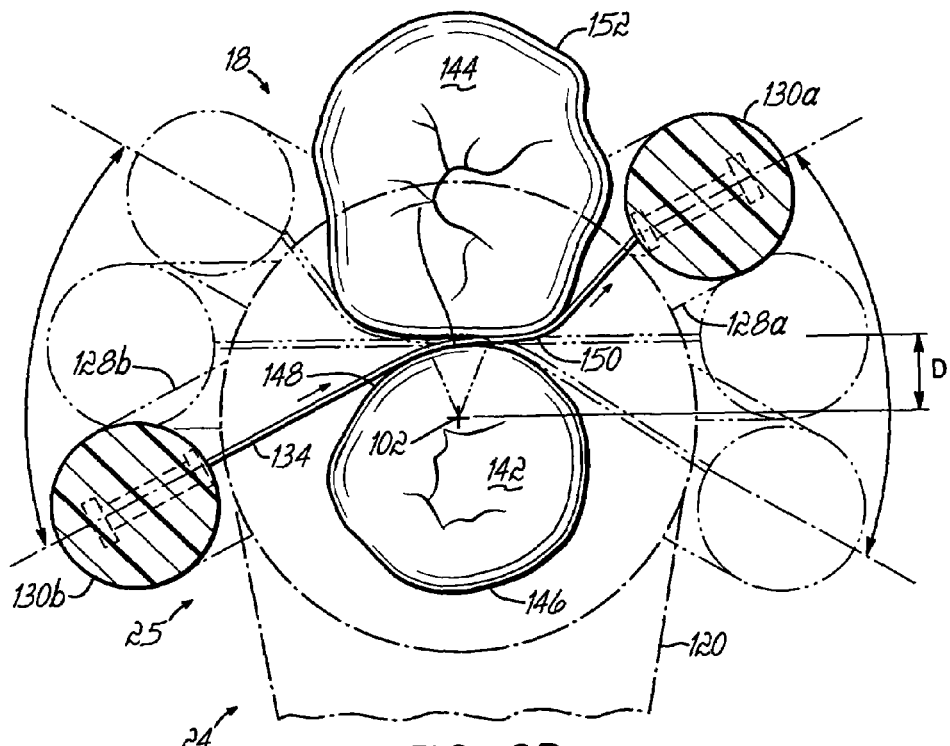
FIG. 6C and FIG. 6D are top plan views, partially in cross section, illustrating the translatory rubbing action which occurs simultaneously with the oscillating action of the flossing material in the use of the flossing head of FIG. 5.
Figure 6C:
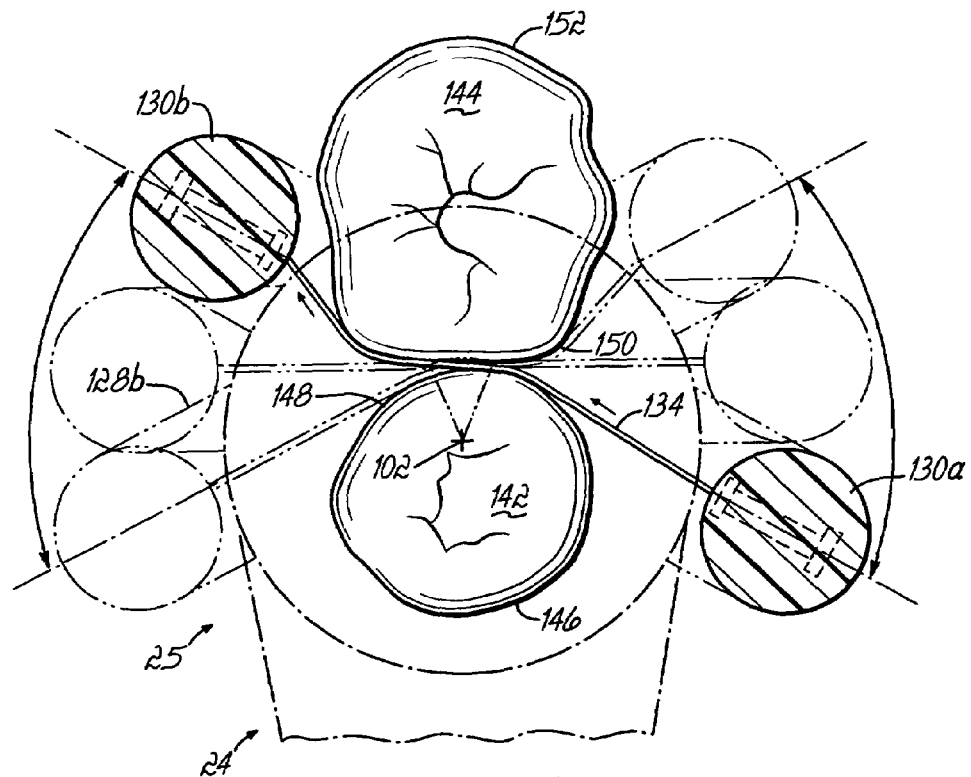

With reference to FIGS. 6C and 6D, there is illustrated in greater detail, the translatory rubbing action which occurs simultaneously with the oscillatory arcuate rotational movement of the flossing material as a result of the offset of the center 160 of the strip of flossing material 134 from the axis of rotation 102 about which the flossing head oscillates. This rubbing action, or so-called "shoe shine effect", results in the flossing material wrapping about and rubbing against the facing surfaces 142a, 144a of adjacent teeth, as well as the front side 146 of a first tooth 142 and the rear side 152 of an adjacent tooth 144 followed by the flossing material rubbing in the opposite direction against the facing surfaces 142a, 144a and the front surface 150 of the adjacent tooth 144 and the rear surface 148 of the first tooth 142 as the flossing material 134 oscillates and translates from the positions illustrated in solid and phantom lines in FIGS. 6C and 6D.

It has been found that an offset D of approximately 1/10 of an inch results in a very satisfactory translatory rubbing action of the floss material during the oscillation of the flossing head through an arcuate motion of approximately 45 angular degrees. This offset distance D, though, may vary, but it has been found that too much variance results in too little translatory or rubbing motion if the offset is much less than approximately 0.08 inches or too much translatory or rubbing motion if the offset distance D is greater than approximately 0.125 inches.

In a preferred embodiment, the flossing head 18 and its integral yoke 126 are made from a flexible polyester plastic such that the tines of the yoke may flex slightly to absorb shock and enable the flossing material retained between the tines to better wrap about teeth during the flossing process as explained hereinabove.

The speed with which the flosser head 18 rotates in an oscillatory manner may vary as desired. The flosser head 18 preferably oscillates back and forth in an arc at a frequency of between 2,000 and 3,000 cycles per minute. In one preferred embodiment, the tines oscillate at a frequency of 2,800 cycles per minute. A cycle is defined as the movement of the tines between a first end position shown in FIG. 6A to a second end position illustrated in FIG. 6B and back to the first end position. When viewed in front elevation as illustrated in FIGS. 5 and 9A, this rapid or high frequency oscillation of the flossing material 134 and flossing tines 128*a* and 128*b* has the appearance of an X-shaped blur, sometimes colloquially referred to as the "X factor" movement of the flossing material.

In one preferred embodiment, the flosser head 18 includes a cup-shaped toothpaste holder 136 having a generally truncated conical shape. As shown in FIG. 3, the toothpaste holder 136 has a bottom wall 138 and a sidewall 140 having an upper edge 141. However, other shapes and configurations may be utilized as desired. The toothpaste holder 136 is preferably made of food grade latex or polyurethane or any other soft flexible plastic material. It is also envisioned that the cup-shaped toothpaste holder could have ripple-shaped projections on the outer edge of the holder so as to enhance brushing actions during use of the flossing procedure.

In use, an operator grabs the handle portion 22 of the motorized flosser 10 and then pushes the button 54 upwardly towards the flosser head 18. Movement of the button 54 activates the motor 48, thereby rotating the flossing head 18 in an oscillatory manner at a predetermined frequency. The user then presses the length of flossing material 134 between adjacent teeth while the flossing head 18 is oscillating arcuately and preferably simultaneously, translating back and forth across the face of the teeth as a result of the offset D of the flossing material from the axis of rotation about which it is oscillated. A bite pad 135 is secured to the rear of the stem 24 and, more particularly, to the rear housing piece 92 of the neck section of the stem 24. The user may bite down on the bite pad 135 to leverage the length of flossing material 134 between the teeth. The oscillating motion moving the tines of the flosser head in an arc causes the length of flossing material to easily enter between adjacent teeth and to wrap around and contact a front part of a first tooth and a rear part of a second tooth adjacent the first tooth. Then, as part of the same cycle, the length of flossing material is wrapped around and contacts a rear part of the first tooth and a front part of the second tooth. And, to floss a greater surface of the teeth, the floss may be slightly pressed or pulled against a tooth surface while the flossing head continues to oscillate or translates and oscillates.

If desired a user may insert toothpaste (not shown) into the toothpaste holder 136 prior to using the motorized flosser 10. The toothpaste (not shown) enables the length of flossing material 134 to more easily pass between adjacent teeth and further provides additional cleaning of the teeth.

With reference now to FIGS. 10, 10A, 10B and 11, there is illustrated a second embodiment of the stem portion and flossing head of the motorized flosser of FIG. 1. This second embodiment incorporates a different stem portion 200 of the body or so-called stem, as well as a different flosser head 202 and drive assembly 204 for interconnecting the reciprocable drive link 70 of the lower handle portion of the flosser to the flosser head 202. This stem or upper end portion 200 of the body is intended to be substituted for the upper stem portion 24 of the motorized flosser of FIG. 1. The remainder of that flosser 10, including particularly the lower handle portion 12, remains the same with the result that this new stem 200 of the flosser may be used in combination with that motorized handle portion 12 or with any other conventional motorized handle body which has a reciprocating output linkage element similar to linkage element 70.

The stem portion or stem 200 of the body has a hollow, generally inwardly tapered lower neck section 206 and an outwardly tapered upper end section 208 terminating in a generally cylindrical upper head section 210. As may be seen most clearly in FIG. 11, the stem is a unitary molded plastic part made in one embodiment from a blend of polyester and polycarbonate plastic. The front side of the cylindrical head 21 of the stem 200 is generally open and the back side closed. Located in the upper tapered end section of the stem 200, there is a generally triangular-shaped opening 212 (shown in hidden lines in FIG. 11) within which there is located a cap 214. As explained more fully hereinafter, the purpose of this opening 212 and cap 214 is to permit of convenient molding and assembly of the stem section of the flosser. After assembly of the stem drive assembly 204 and flossing head 202, the cap 214 is fixedly secured in the opening 212 to form a unitary stem assembly 220 adapted to be removably and drivingly attached to the motorized lower handle portion of the motorized flosser.

Figure 11:
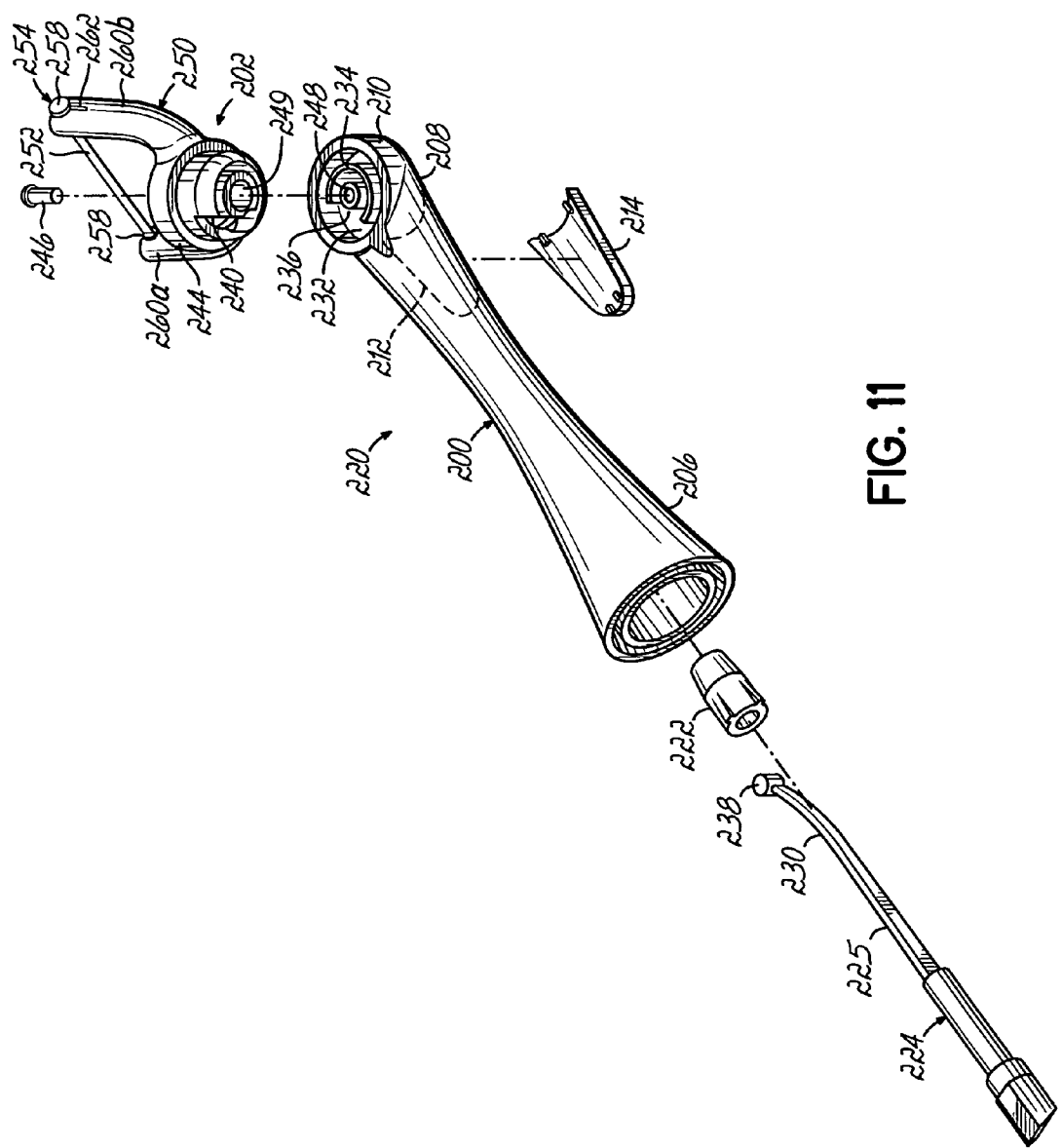
FIG. 11 is an exploded perspective disassembled view of the upper stem portion of the body illustrated in FIG. 10.
Figure 11A:
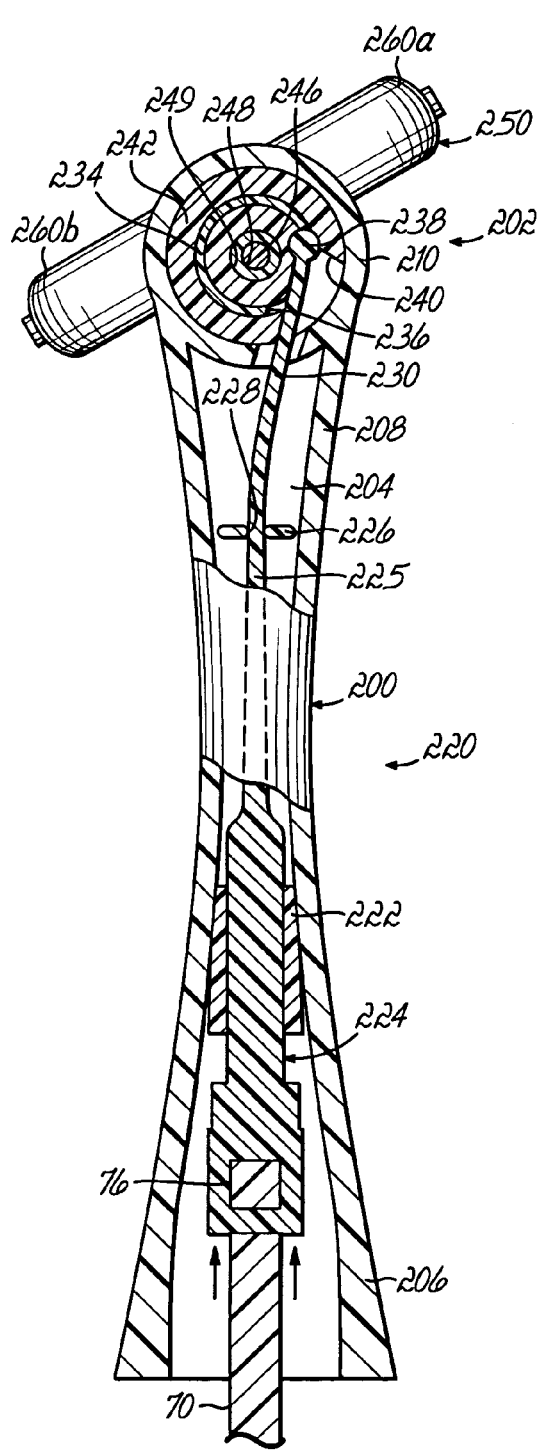
FIG. 11A is a cross sectional view of the upper stem portion of the flosser of FIG. 10 illustrating the flosser head in one extreme position of its arcuate oscillatory movement.
Figure 11B:
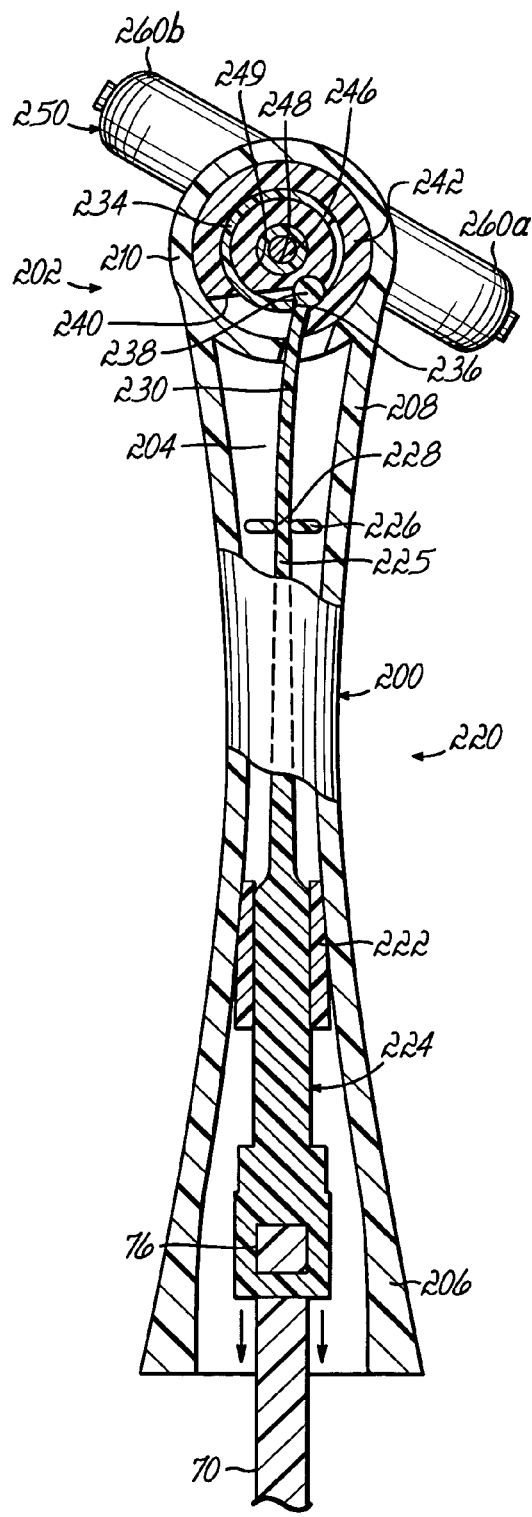
FIG. 11B is a cross sectional view similar to FIG. 11A, but illustrating the flosser head in its other extreme position of arcuate oscillatory movement.

As may be seen most clearly in FIGS. 11A and 11B, there is a tapered guide sleeve 222 fixedly received within the tapered interior cavity of the lower section 206 of the stem 200. This guide sleeve 222 functions as a guide for the lower end of a reciprocably movable flexible drive rod 224. There is also an upstanding rib 226 molded onto the interior surface of the neck section of the stem, which rib 226 has a slot 228 formed therein. This slot 228 functions as a guide for the upper end 230 of the flexible drive rod 224. Molded into and upstanding from the rear wall 232 of the cylindrical head section 210 of the stem 200, there is an arcuate rib or flange 234 which extends through a circular arc of about 315 degrees leaving a gap 236 of approximately 45 degrees between the opposed ends of the rib. A bulbous end 238 on the upper end of the drive rod 224 is located within this gap and is received within a recess 240 of a drive disc portion 242 of the flossing head 202. This drive disc portion 242 is molded into and forms a portion of the base 244 of the flossing head 202.

The unitary molded flossing head, including its driving disc portion and cylindrical base section are maintained in an assembled relationship by a rivet 246 (see FIG. 10) which extends from the back or rear side of the rear wall 232 of the cylindrical head section 210 of the stem 200, through a cylindrical rib 248 of the head section, through a center hole 249 of the flossing head 202 to the front side of the flossing head 218. The rivet 246 is headed at both ends to maintain the assembled relationship between the head section of the stem and the unitary drive disc and flossing head.

In order to assemble the flossing head stem and drive mechanism contained within the stem, the flexible drive rod 224 is first pushed upwardly through the hollow interior of the stem 200 and through the guide sleeve 222. Because the cap 214 is, at this point of time, absent from the opening 212, the thin flexible upper section 225 of the drive rod 224 is positioned into the slot or recess 228 of the rib 226. Thereafter, the cap 214 is positioned in the opening 212 and permanently secured therein. The drive disc portion 242 of the flossing head is then inserted into the open front cavity of the head portion of the stem, thereby locating the upper bulbous end 238 of the drive rod 224 in driving engagement with the drive disc portion of the flossing head. The rivet 246 is then inserted and the head of the end of the rivet squeezed so as to permanently attach the flossing head 218 to the head end of the stem 200. As thus assembled, the stem assembly 220 may be attached to the motorized body 12 of the flosser to complete a driving relationship between the motor of the body and the flossing head.

It is important to note that the flexible drive rod 224 is a unitary molded plastic element preferably molded from a flexible plastic material, such as a polyester or acetal plastic. One suitable acetal plastic is marketed as "Delrin". When made from such flexible, non-moisture or toothpaste chemical absorbent plastics, the upper end of the drive rod 224 is sufficiently flexible as to enable the upper end of the rod and particularly, the bulbous upper end to move through an arc as illustrated in the two end positions illustrated in FIGS. 11A and 11B within the recessed cavity 240 of the driving disc portion of the flossing head. If for any reason the flossing head 202 should be abruptly stopped while the motor continues to operate and reciprocate the drive link 70 to which the drive rod 224 is attached, the upper end section 225 of the drive rod 224 will absorb any shock without breakage and flex within the cavity 240 without causing any breakage of any of the drive elements or uncomfortable contact of the flossing head or flossing material with the user's teeth. This flexible drive rod feature, with its flexible drive to the flossing head, functions not only as a shock absorber to prevent breakage of the drive system, but also acts as a safety feature to prevent impact damage to a tooth, as well as damage to gums of a person using the flosser.

Figure 10:
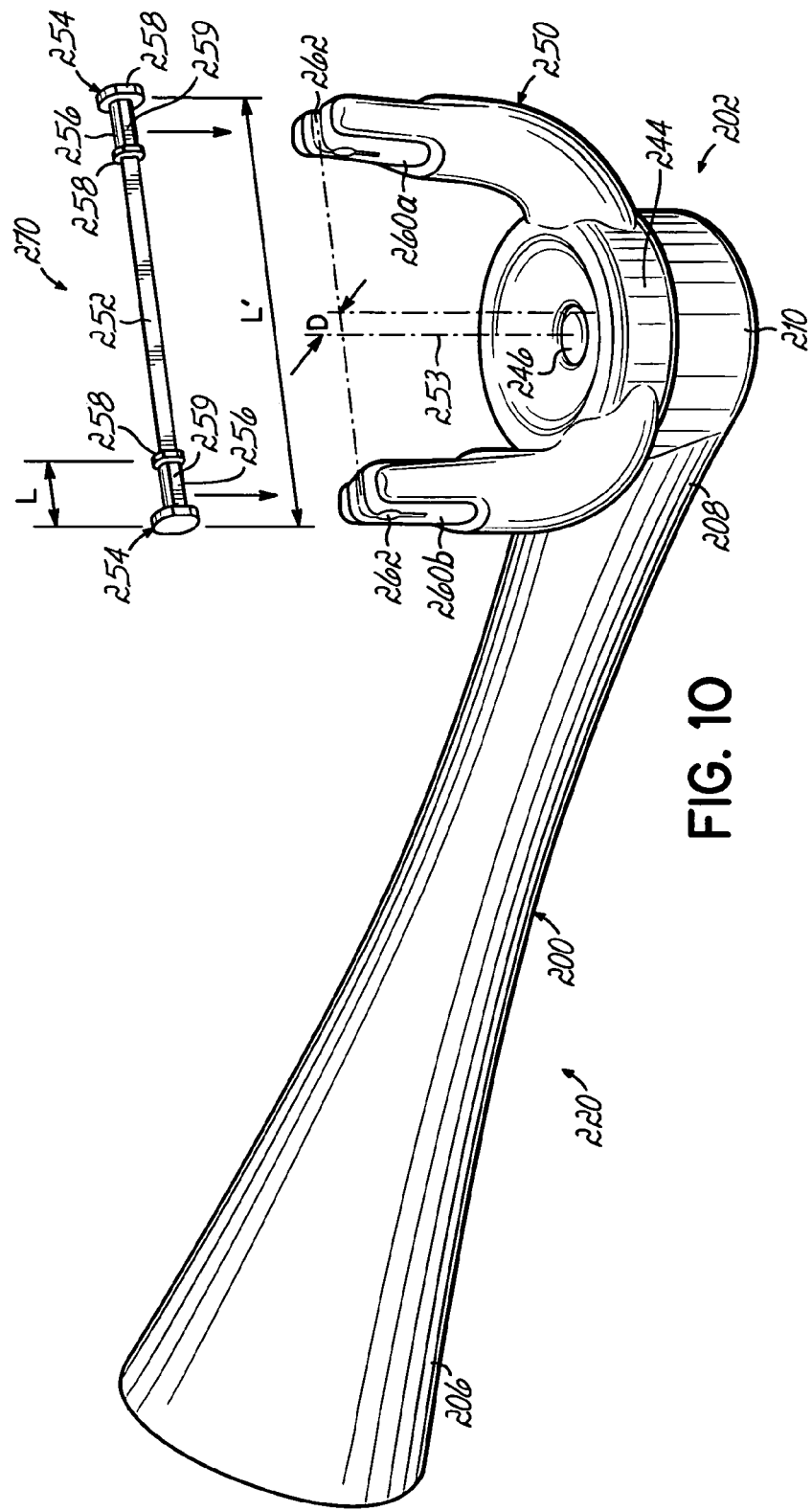
FIG. 10 is a perspective view of a second embodiment of the upper stem portion of the body of the motorized flosser of FIG. 1.

With particular attention now to FIGS. 10 and 11, there is illustrated another substantial difference between flossing head 202 and that illustrated and described in the embodiments of FIGS. 1-9. In this embodiment, as in the embodiment of other flossing heads illustrated and described in FIGS. 5, 9A and 9B, the yoke 250, as well as a section or strip of flossing tape or ribbon 252 mounted on the yoke is offset a distance D from the axis 253 about which the flossing head 202 is oscillating. This embodiment of the flossing head 202 differs principally from the flossing head 18 described earlier in the embodiment of FIGS. 5-9 in that instead of the flossing head being removably attached to the front portion of the motorized flosser, as in the embodiment of FIGS. 1-9, the flossing tape or ribbon 252 with attached snap-in anchors 254 at opposite ends of the section of ribbon is removable and replaceable in the yoke 250 of the flossing head 202.

Figure 12:
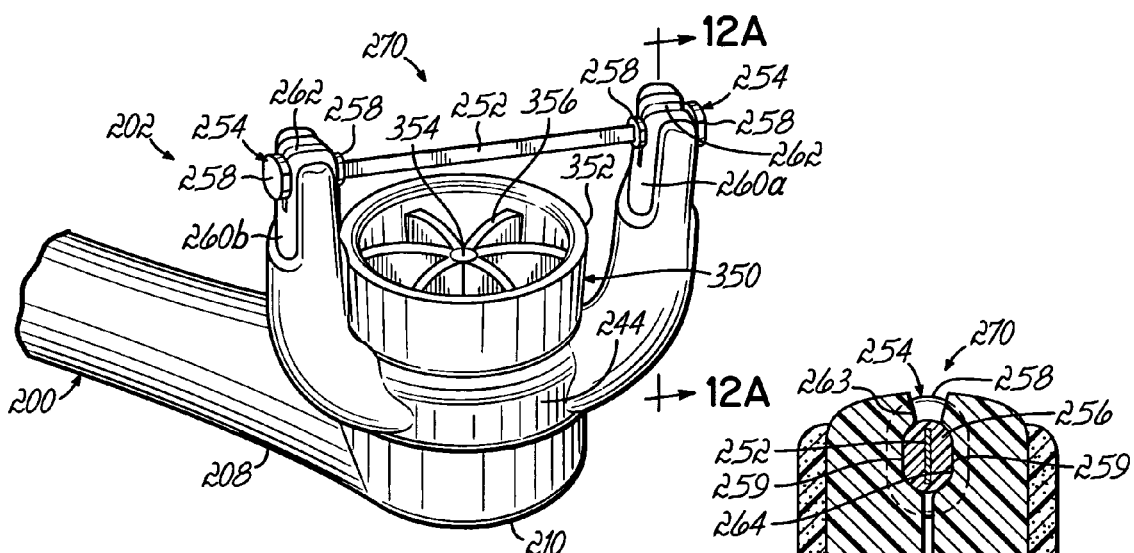
FIG. 12 is a perspective view of another embodiment of the flossing head.
Figure 12A:
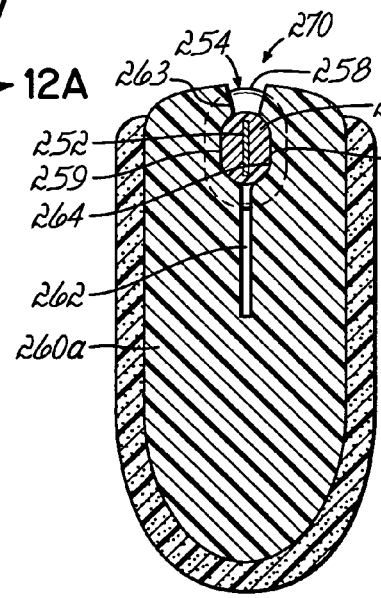
FIG. 12A is a cross sectional view taken on line 12A-12A of FIG. 12.

As may be seen most clearly in FIGS. 10, 12 and 12A, end anchors 254 are made from polypropylene plastic overmolded onto each end of the section of flossing tape 252. These end anchors 254 each have a central section 256 and generally oval or circular end flanges 258 at opposite ends of the central section 254. The central section 256, when viewed in cross section, is generally oval with two flat sides 259 (see FIG. 12A) and rounded ends. As explained more fully hereinafter, the flat sides 259 serve to orient the flossing material tape or ribbon 252 within the tines of the yoke.

The top of each tine 260a and 260b of the yoke 250 has a generally keyhole-shaped slot 262 formed therein into which the anchors 254 are adapted to be snap-fit. Each of these keyhole-shaped slots 262 has opposed flat sections 263 and rounded end sections 264 adapted to receive the similarly shaped cross section of the center portion 256 of an anchor 254 so as to secure and properly orient the flossing tape in the yoke with the tape vertically oriented. The flats 259 on the center section 254 of the anchor are engageable with the flats 241 of the slot such that once snapped into the slot, the anchors, and consequently, the tape, are properly oriented and cannot rotate relative to the yoke.

Figure 15:
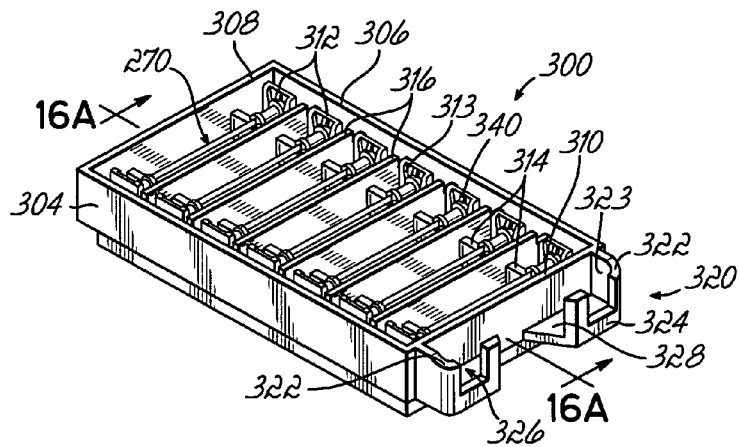
FIG. 15 is a perspective view of a floss carrier cartridge.
Figure 15A:
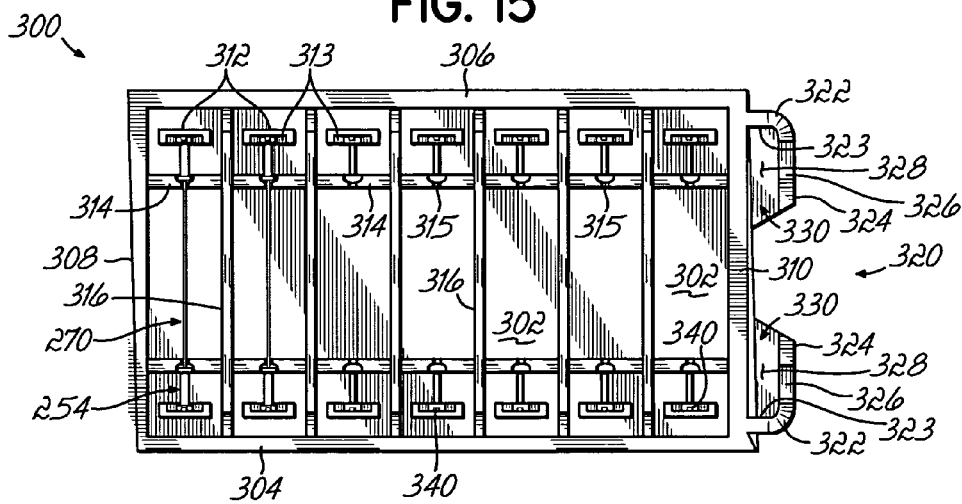
FIG. 15A is a top plan view of the floss carrier cartridge of FIG. 15.

In practice and use of the motorized flosser, whether the flosser utilizes replaceable flosser heads 18 as in the modification of the flosser illustrated in FIG. 1 or replaceable floss carriers 270 (strips of floss 252 with attached anchors 254) as illustrated in the modification of FIGS. 10 and 12, the section or strip of floss material will generally be thrown out and replaced with each use of the flosser. To facilitate storage of multiple new or unused floss carriers 270 and replacement of used floss carriers 270, there is illustrated in FIGS. 15-17 a cartridge 300 particularly suited to this use. The flosser cartridge 300 is a unitary molded plastic cartridge in the form of an open top box having a bottom wall 302 (FIG. 16A) surrounded by two side walls 304, 306 and two end walls 308, 310. Spaced from each of the side walls, there are a number of inwardly facing channels 312 adapted to receive one end 258 of an anchor 254 of one floss carrier 270. Spaced inwardly from the line of channels 312 by a distance slightly greater than the length L (FIG. 10) of an anchor 254, there are a pair of walls 314 extending parallel to the side walls 304 and 306 for the length of the cartridge 300. And extending transversely between the side walls 314, there are spacer walls 316. In the illustrated embodiment, the flosser cartridge 300 is intended to hold seven floss carriers 270, one for each day of the week. When residing within the cartridge, each floss carrier 300 has one anchor 254 located between an inner wall 314 and an upstanding channel 312. As best illustrated in FIG. 16A, the upper end 313 of each of the side walls 313 of each channel 312 is preferably tapered outwardly to facilitate the insertion of the end flange 258 of an anchor 270 into the upper end of the channel 312 to a depth at which the ribbon of floss 252 of each floss carrier 270 is located atop a recess 315 in the top surface of an inner wall 314.

To facilitate removal of a used floss carrier 270 from the yoke 250 of a flossing head 202, there is a floss carrier removal device 320 attached to one end wall 310 of the cartridge 300. This carrier removal device 320 comprises a pair of spaced vertical arcuate end walls 322 which extend outwardly from the end wall 310 and which are spaced apart on their inner surfaces 323 by a distance slightly greater than the length L' (FIG. 10) of the floss carrier 270. These arcuate walls 322 terminate in flat end walls 324 which extend parallel to the end wall 310. Rectangular recesses 326 extend downwardly from the top edge of the vertical walls 324 to facilitate insertion of the tines 260a and 260b of the yoke 250 of a flossing head into the removal device 320. A bottom wall 328 extends between the end wall 310 and the spaced vertical walls 324.

Figure 16A:
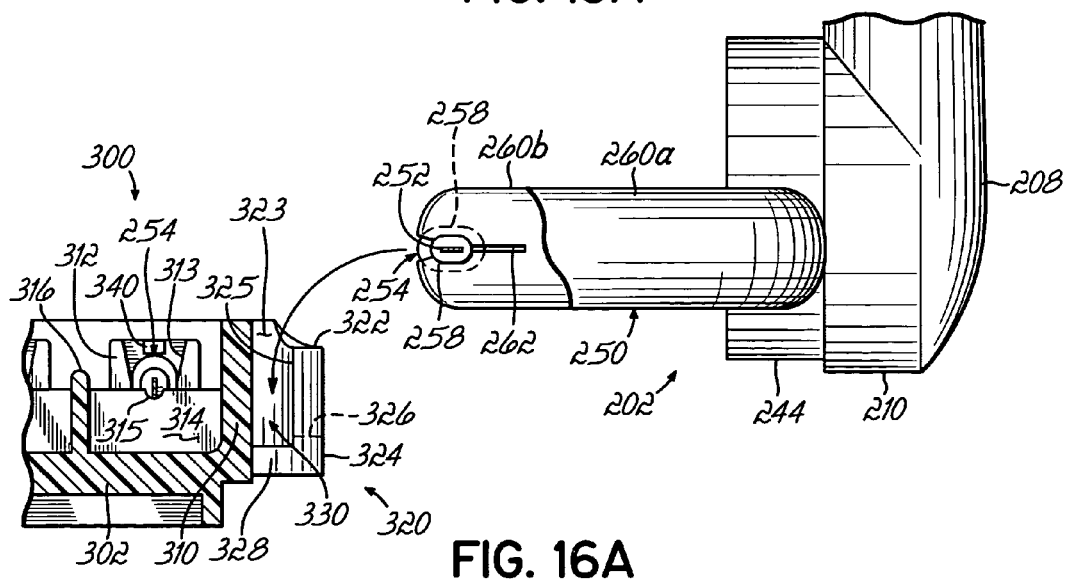
FIGS. 16A, 16B, 16C, 16D, 16E an 16F are side elevational views of a portion of the cartridge of FIG. 15 illustrating in sequential views how that cartridge is used to extract a used floss carrier from the yoke of a flossing head.
Figure 16B:
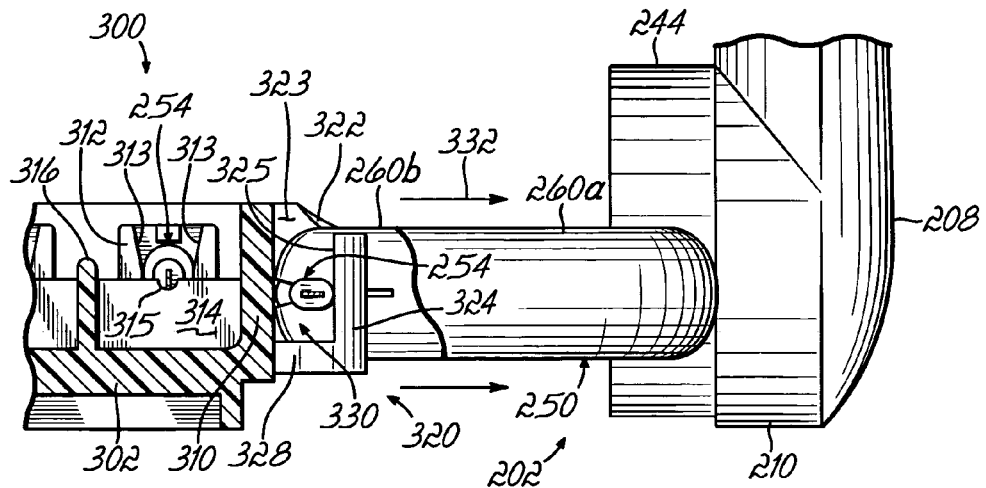
Figure 16C:
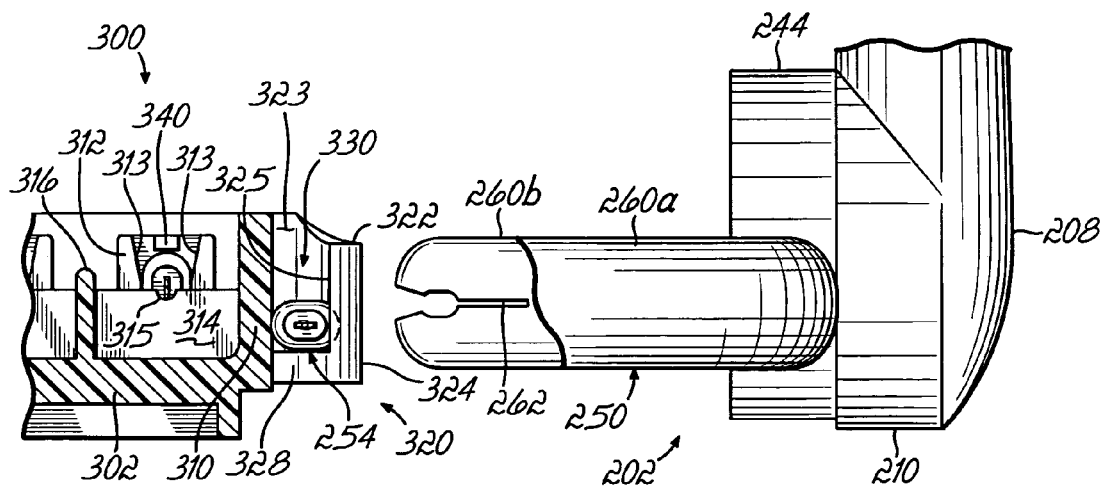
Figure 16D:
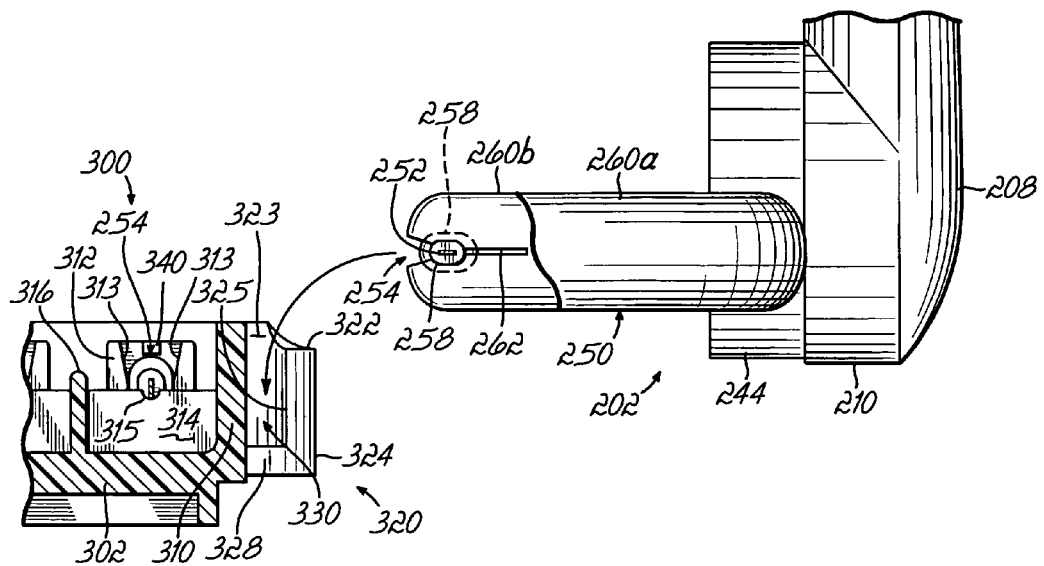
Figure 16E:
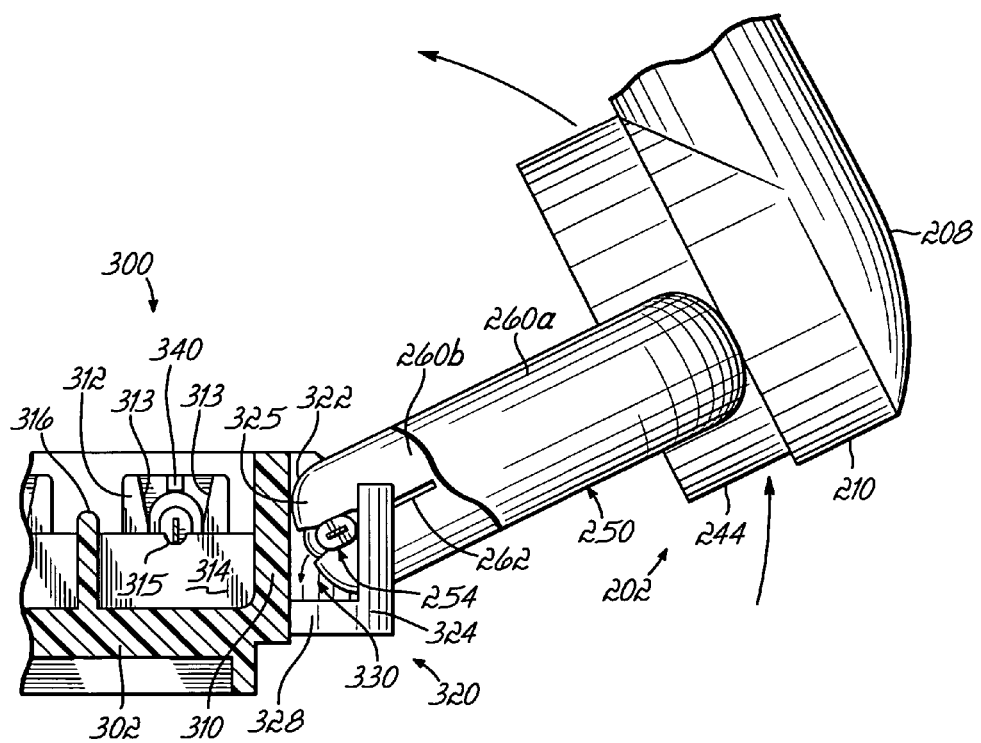
Figure 16F:
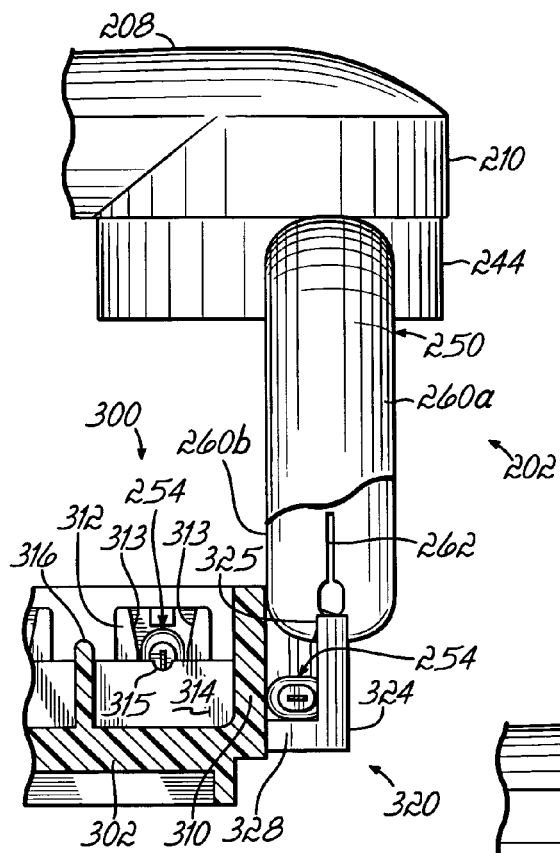
Figure 17:
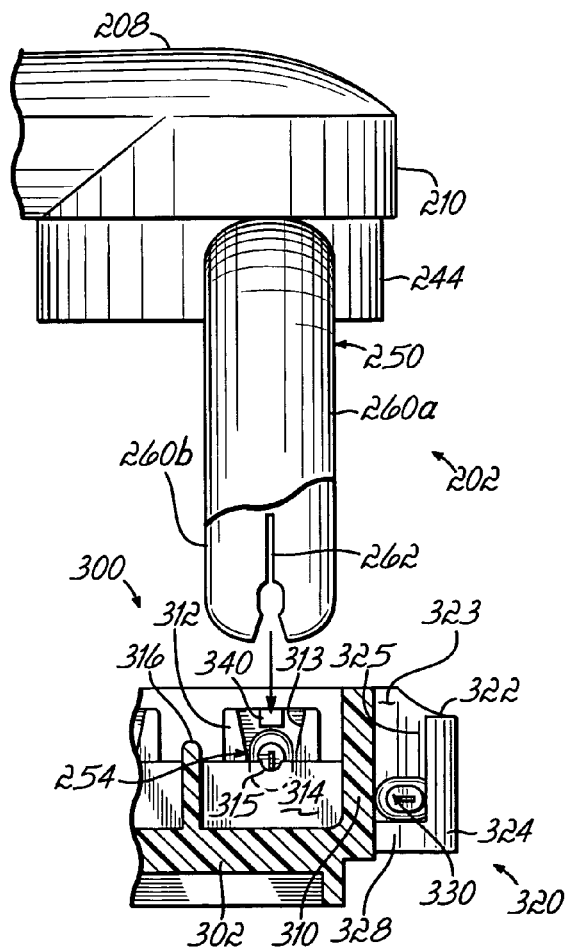
FIG. 17 is a side elevational view, partially broken away, of a portion of the cartridge of FIG. 15 illustrating how that cartridge is used to insert a new floss carrier into the yoke of a flossing head.

With reference now to FIGS. 16A and 16B, it will be seen that in order to remove a used floss carrier 270 from the yoke 250 of a flossing head 202, the tines 260a and 260b of a flossing head 202 may be inserted into the recesses 326 of the carrier removal device 320 on the cartridge 310. This is done by moving the yoke downwardly into these spaced recesses 326. The width W of the recesses 326 is approximately the same as the length of the center portion 256 of the anchors 254, such that the end flanges 258 of the anchors 254 rest against the inside surface 325 of the vertical wall 324 when the ends of the tines 260a and 260b are located within the recesses 330 behind the vertical walls 324. If the yoke, after placement of the tines and the used floss carrier 300 into the cavity 330 behind the end wall 324 is then pulled outwardly away from the cartridge as indicated by the arrows 332 of FIG. 16B, the floss carrier 270 will, as illustrated in FIG. 16C, be left within the cavity 330 behind the end walls 324 as a result of the opening of the snap-fit engagement between the anchors 254 of the floss carrier and the slots 262 in the tines of the yoke 250. Or, alternatively to a straight pull of the yoke away from the cartridge to disengage the floss carrier 270 from the yoke 250, the complete handle of the motorized flosser may be rotated as illustrated in FIGS. 16C-16F about the longitudinal axis 30 of the complete motorized flosser to disengage the floss carrier 270 from the yoke and leave it deposited in the cavity 330 of the flosser cartridge removal device 320.

Figure 18:
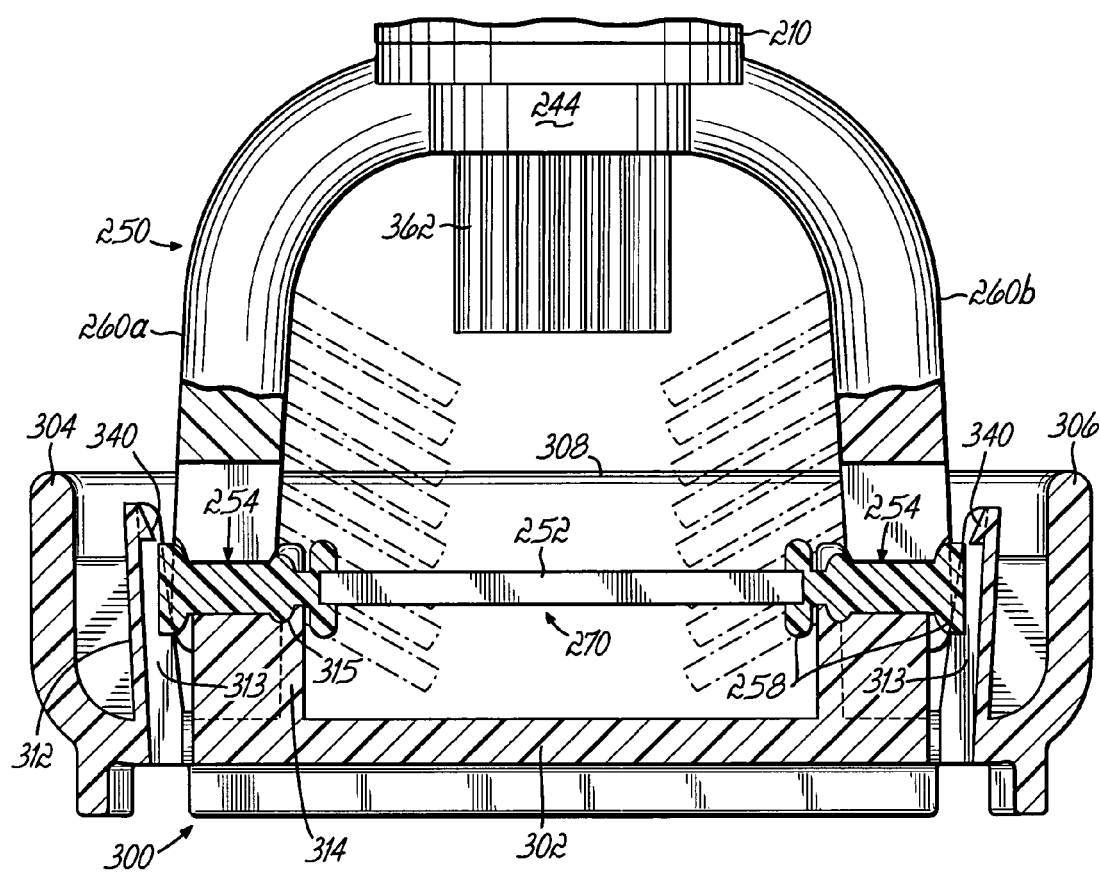
FIG. 18 is an enlarged cross sectional view taken on line 18-18 of FIG. 17.

In order to insert a new or replacement floss carrier 270 from the cartridge 300 into the yoke 250 of a flossing head 202, all that is required as illustrated in FIGS. 17 and 18 is for the flosser head 250 to be moved downwardly into the carrier with the ends of the tines 260a and 260b placed between the vertical channels 312 on opposite sides of the cartridge 300. When the yoke is moved downwardly in this position, the ends of the tines act as cams to engage the walls 313, 314 and move hooks 340 formed on the walls 313 and 314 outwardly (see FIG. 18) while the slots 262 of the tines of the yoke snap-fit into engagement with the anchors 254 on opposite sides of the ribbon of tape 234 of the new floss carrier 300. Having made this snap-fit engagement, and with the hooks 340 displaced outwardly away from engagement with the flanges 258 of the anchors 254, the yoke and the flosser head is moved upwardly, thereby withdrawing the new floss carrier 270 from the cartridge 300 with the new floss carrier ready for use in the flosser.

With reference now to FIG. 12, there is illustrated another embodiment of the flossing head 202. In this embodiment, the flossing head 202 has mounted between the tines 260a and 260b a flexible toothpaste receiving cup 350. This cup has a bottom (not shown) from which there extends upwardly a cylindrical wall 352. The top of this cup is open such that toothpaste may be placed within this cup which is fixedly secured to the top surface of the base 244 of the flossing head 202. Preferably, there is a center post 354 extending upwardly from the bottom of the flexible cup 350 and radial baffles 356 which extend between the center post 354 and the side wall 352. These baffles 356 are provided to enhance the effectiveness of toothpaste contained within the cup when the motorized flosser incorporating this flossing head is utilized to floss and brush the teeth of a person using the flosser.

Figure 13:
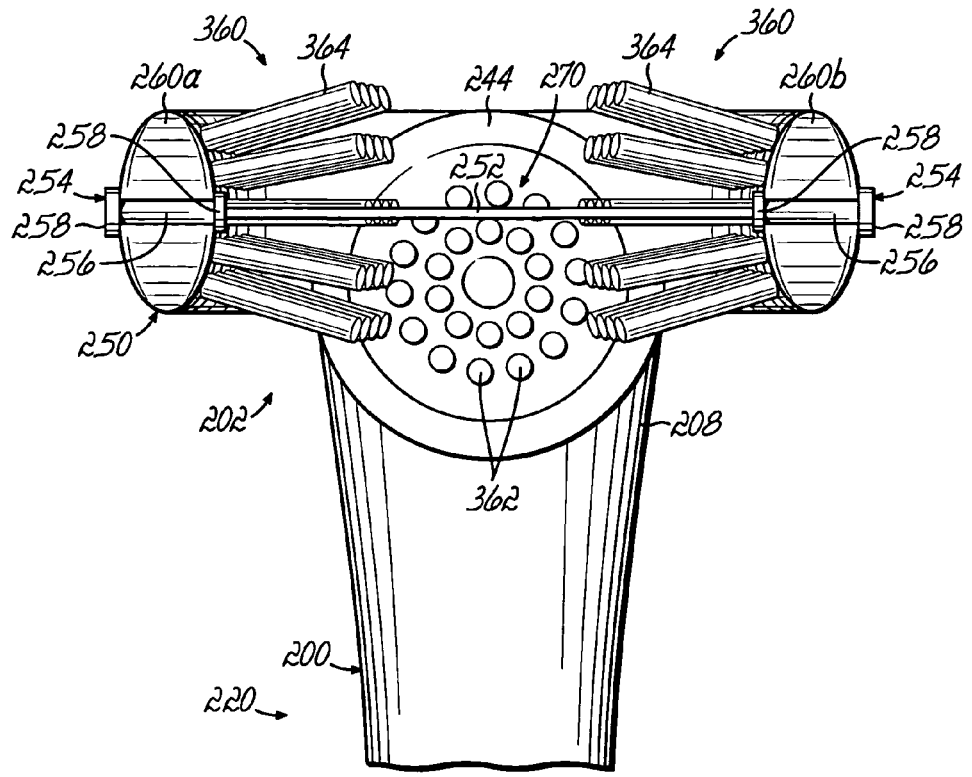
FIG. 13 is a front elevational view of another embodiment of the flossing head.
Figure 14:
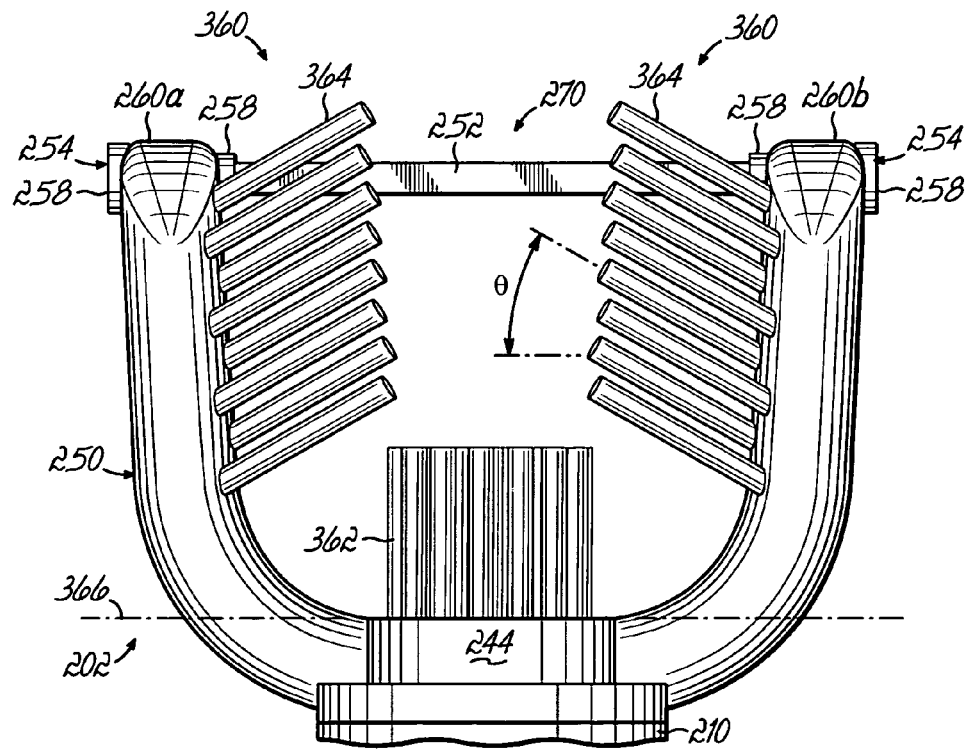
FIG. 14 is a side elevational view of the flossing head of FIG. 13.

With reference now to FIGS. 13 and 14, there is illustrated yet another embodiment of a flossing head 202 utilizable in the practice of this invention. This flossing head is substantially identical to the flossing head 202 of FIGS. 10 and 11 except that it adds to that flossing head toothbrush bristles 360 to enable the flosser to simultaneously floss teeth and brush them. To that end, bristles 362 are mounted on the base 244 of the flossing head 202 and extend upwardly therefrom. Additionally, bristles 364 are mounted on the tines 260a and 260b. These bristles 364, as illustrated in FIG. 13, extend inwardly between the tines from one tine toward the other and upwardly at an angle θ of approximately 30 degrees to a plane 366 through the base 244 of the flossing head 202. This angulation of the bristles affects a more effective brushing action, as well as a simultaneous flossing action, upon oscillation of the flossing head 202 as explained hereinabove when that flossing head is oscillated rapidly through approximately a 45 degree angular oscillation.

Figure 19A:
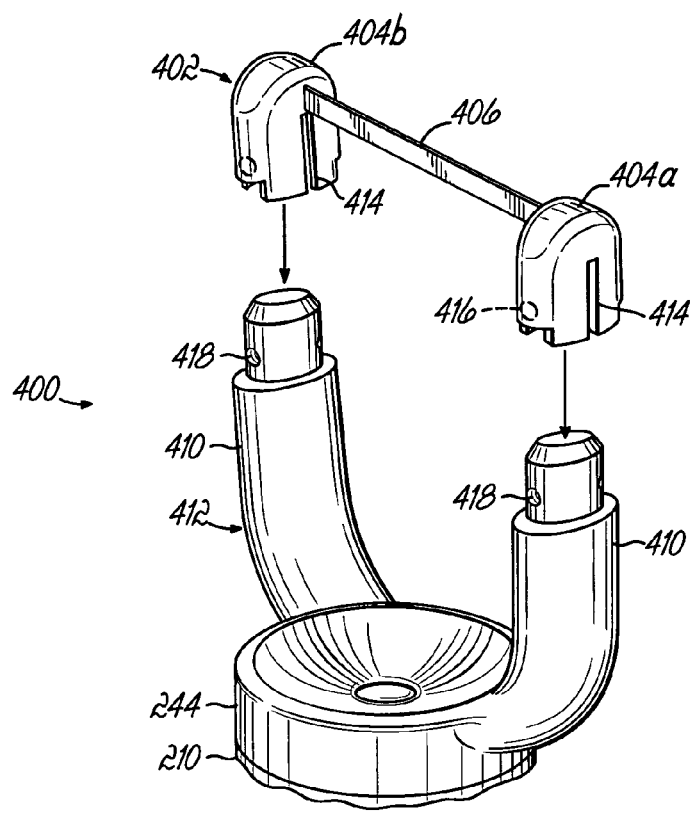
FIG. 19A is an exploded perspective view of another embodiment of the flossing head.
Figure 19B:
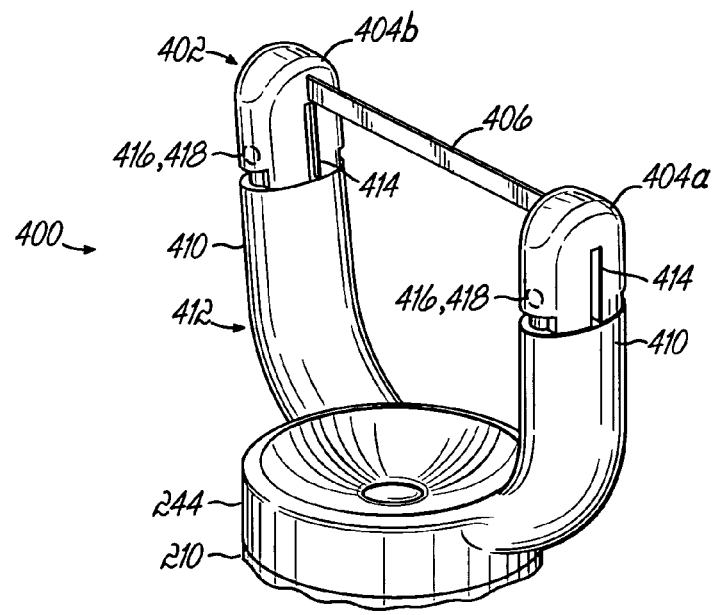
FIG. 19B is a perspective assembled view of the flossing head of FIG. 19A.

With reference now to FIGS. 19A and 19B, there is illustrated another embodiment of a flossing head utilizable with the stem 200 of FIG. 10. This embodiment of flossing head 400 is similar to the flossing head 202 of FIG. 10 in that it incorporates removable and replaceable carrier 402 rather than removable and replaceable flosser heads as in the embodiment of flosser illustrated in FIGS. 1-9. In this embodiment, the carrier 402 has end caps 404a and 404b molded onto opposite ends of a strip or ribbon of flossing material 406. These end caps have a downwardly facing hollow interior cavity which fits over and snaps onto end portions 408 of the tines 410 of the yoke 412 of the flossing head 400. The end caps 402 preferably have downwardly open slots 414 in the side walls of the caps to enable the side walls of the caps to spread apart when the caps are forced downwardly over the ends 408 of the tines and a protrusion (shown in phantom in FIG. 19A) on the inside of the cap is snap-fit onto a recess 418 formed in the side of the upper portion 408 of the tines 410. Thereby, the replaceable carrier 402 may be removably and replaceably snap-fit onto the tines of the yoke of the flossing head 400.

While we have described several different embodiments of our invention, it is to be understood that various changes and modifications may be made to the embodiments described and discussed hereinabove without departing from the scope of the present invention, which is defined by the following claims and equivalents thereof.

We claim:

1. A motorized flosser comprising:
   a generally hollow elongated body having opposed first and second ends aligned along a longitudinal axis;
   a power supply located within the hollow portion of the elongated body;
   a flosser head having a base connected to a front side of the first end of the elongated body;
   a yoke extending from the base of the flosser head, said yoke having a pair of spaced tines between which extends a piece of flossing material;
   a drive assembly including a flexible drive element interconnecting said power supply to the flosser head such that activation of the power supply causes arcuate oscillation of the flosser head and flexible flossing material about an axis of oscillation, wherein the axis of oscillation is offset from the piece of flossing material extending between the spaced tines in a direction generally parallel to the longitudinal axis.

2. The motorized flosser of claim 1 wherein said flexible drive element is a flexible drive rod made of plastic material.

3. The motorized flosser of claim 2 wherein said flexible drive rod is made of a polyester or acetal plastic material.

4. The motorized flosser of claim 2 wherein said yoke is made of a polyester plastic material.

5. The motorized flosser of claim 1 wherein said yoke is made of a flexible plastic material.

6. The motorized flosser of claim 5 wherein said yoke is made of a polyester plastic material.

7. The motorized flosser of claim 1 wherein a distance of each tine relative to the axis of oscillation is fixed.

8. A motorized flosser comprising:
   a generally hollow elongated body having opposed first and second ends;
   a power supply located within the hollow portion of the elongated body;
   a flosser head having a base connected to a front side of the first end of the elongated body;
   a yoke extending from the base of the flosser head, said yoke having a pair of spaced tines between which extends a piece of flossing material, said yoke being made of a flexible plastic material, wherein the flosser head further comprises a flexible toothpaste holder located between said spaced tines of said flosser head; and a drive assembly interconnecting said power supply to the flosser head such that activation of the power supply causes arcuate oscillation of the flosser head and flexible flossing material.

9. The motorized flosser of claim 8 wherein the toothpaste holder is generally cup-shaped with an open side toward the flossing material.

10. The motorized flosser of claim 9 which further includes baffles located in said cup-shaped toothpaste holder.

11. The motorized flosser of claim 8 further comprising a bite pad secured to a rear side of said first end of said elongated body.

12. The motorized flosser of claim 8 wherein the power supply includes a motor and a battery.

13. The motorized flosser of claim 8 wherein the flosser head oscillates at a sufficiently high frequency when said power supply is turned on so as to create a visual blur in the shape of an X when viewed from the front side of said elongated body.

14. The motorized flosser of claim 13 wherein the flosser head oscillates at a frequency of between 2,000 and 3,000 cycles per minute.

15. The motorized flosser of claim 8 wherein the flosser head oscillates through an arc of between 30 and 75 degrees.

16. The motorized flosser of claim 8 wherein the flosser head oscillates through an arc of approximately 45 degrees.

17. A motorized flosser comprising:
a generally hollow elongated body having opposed first and second ends aligned along a longitudinal axis;
a power supply located within the hollow portion of the elongated body;
a flosser head having a base connected to a front side of the first end of the elongated body;
a yoke extending from the base of the flosser head, said yoke having a pair of spaced tines between which extends a piece of flossing material;
a drive assembly including a flexible drive rod interconnecting said power supply to the flosser head such that activation of the power supply causes arcuate oscillation of the flosser head and flexible flossing material about an axis of oscillation, wherein the axis of oscillation is offset from the piece of flossing material extending between the tines in a direction generally parallel to the longitudinal axis.

18. The motorized flosser of claim 17 wherein said generally elongated hollow body comprises a handle portion and a stem portion, said power supply including a drive motor located in said handle portion;
said stem portion comprising a first end section connected to said handle portion of said body and a second end terminating in a head section, said head section having a drive disc located therein;
a drive linkage in said handle portion of said body, said drive linkage including a linearly reciprocable drive link operably connected to said drive motor; and
said flexible drive rod being located in said stem portion of said body, said flexible drive rod being connected at one end to said linearly reciprocable drive link and at the opposite end to said drive disc.

19. The motorized flosser of claim 18 wherein said drive disc is operatively connected to said flosser head so that arcuate oscillatory movement of said drive disc effects a corresponding arcuate oscillatory movement of said flosser head.

20. The motorized flosser of claim 19 wherein said drive disc is formed as a unitary portion of said flosser head.

21. The motorized flosser of claim 19 wherein said drive disc is formed as a separate element from said flosser head.

22. A motorized flosser comprising:
a generally hollow elongated body having opposed first and second ends;
a power supply located within the hollow portion of the elongated body;
a flosser head mounted upon a front side of said first end of the elongated body, said flosser head being drivably connected to said power supply by a drive mechanism operative to effect arcuate oscillatory motion of said flosser head about an axis of oscillation;
said flosser head comprising a base and a yoke, which yoke includes a pair of spaced tines extending forwardly from the base and a piece of floss material extending between the tines; and
said piece of floss material being offset from said axis of oscillation of said head such that upon activation of said power supply, said piece of floss material is simultaneous arcuately oscillated and moved in a translatory back and forth motion.

23. The motorized flosser of claim 22 wherein the center of said piece of floss material is offset from said axis of oscillation by an offset distance between approximately 0.08 inches to approximately 0.125 inches.

24. The motorized flosser of claim 23 wherein said offset distance is approximately 1/10 inches.

25. The motorized flosser of claim 22 wherein a distance of each tine relative to the axis of oscillation is fixed.

26. The motorized flosser of claim 22 wherein the flosser head oscillates at a sufficiently high frequency when said power supply is turned on so as to create a visual blur in the shape of an X when viewed from the front side of said elongated body.

27. A motorized flosser comprising:
a generally hollow elongated body having opposed first and second ends;
a power supply located within a hollow portion of the elongated body;
a flosser head having a base connected to a front side of the first end of the elongated body, said flosser head being angularly oscillatable about a fixed axis;
a yoke extending from the base of the flosser head, said yoke having a pair of spaced tines between which there extends a piece of flossing material; and
said piece of flossing material being offset from said fixed axis of oscillation of said flosser head such that upon oscillation of said flosser head, said pieces of flossing material is simultaneously arcuately oscillated and moved in a translatory back and forth motion.

28. The motorized flosser of claim 27 wherein the center of said piece of floss is offset from said axis of oscillation by an offset distance between approximately 0.08 inches to approximately 0.125 inches.

29. The motorized flosser of claim 28 wherein said offset distance is approximately 1/10 inches.

30. The motorized flosser of claim 27 wherein a distance of each tine relative to the axis of oscillation is fixed.

31. The motorized flosser of claim 30 wherein the flosser head oscillates at a sufficiently high frequency when said power supply is turned on so as to create a visual blur in the shape of an X when viewed from the front side of said elongated body.

32. A method of flossing teeth with a motorized flosser having a flossing head including a pair of tines between which there extends a length of flossing material, said flossing head being arcuately oscillatable about a fixed axis and said length of flossing material being offset from said fixed axis, said method comprising:

activating the motorized flosser so that the flossing head oscillates arcuately about said fixed axis and said length of flossing material oscillates arcuately and simultaneously translates back and forth;

moving said flossing material between adjacent teeth while the motorized flosser is so activated.

33. The method of claim 32 wherein the tines of the flossing head and the flossing material move arcuately through an arc of approximately 45 degrees during each oscillatory cycle of the flossing head.

34. The method of claim 32 wherein the tines of the flossing head and the flossing material move arcuately through an arc of between 30 and 75 degrees during each oscillating cycle of the flossing head.

35. The method of claim 32 wherein the flossing head oscillates at a frequency between 2,000 and 3,000 cycles per minute.

36. A method of flossing teeth with a motorized flosser having a flossing head including a pair of tines between which there extends a length of flossing material, said flossing head being arcuately oscillatable about a fixed axis and said length of flossing material being offset from said fixed axis, said method comprising:

activating the motorized flosser so that the flossing head oscillates arcuately about said fixed axis and said length of flossing material oscillates arcuately and simultaneously translates back and forth;

moving said flossing material between adjacent teeth while the motorized flosser is so activated; and inserting toothpaste into a toothpaste holder secured to the flosser head prior to activating the motorized flosser such that the teeth are cleaned by the toothpaste and the flossing material while simultaneously being flossed and polished by the oscillating and translatory flossing material.

37. A method of removing plaque and biofilm from the surface of teeth comprising:

activating a motorized flosser having a flossing head so that the flosser head of the motorized flosser oscillates arcuately about a fixed axis;

pressing a length of flossing material extending between and secured to two tines of the flossing head between adjacent teeth while the flossing head continues to oscillate arcuately and the length of flossing material oscillates arcuately and simultaneously translates back and forth to both floss and polish the teeth between which the length of flossing material is pressed; and placing toothpaste upon bristles mounted upon the flossing head before activating the motorized flosser.

38. The method of claim 37 which further comprises moving said flossing material toward and away from adjacent teeth while the flossing material continues to oscillate between the adjacent teeth by gently pressing and pulling the flossing material toward and away from one of the adjacent teeth.

39. A method of removing plague and biofilm from the surface of teeth comprising:

activating a motorized flosser having a flossing head so that the flosser head of the motorized flosser oscillates arcuately about a fixed axis;

pressing a length of flossing material extending between and secured to two tines of the flossing head between adjacent teeth while the flossing head continues to oscillate arcuately and the length of flossing material oscillates arcuately and simultaneously translates back and forth to both floss and polish the teeth between which the length of flossing material is pressed;

placing toothpaste upon bristles secured to the tines of the flossing head before activating the motorized flosser so that the flosser is operative when activated to simultaneously brush the teeth with the bristles and to floss and polish the teeth with the flossing material.

40. A method of flossing teeth with a motorized flosser having a flossing head including a pair of tines between which there extends a length of flossing material, said flossing head being arcuately oscillatable about a fixed axis and said length of flossing material being offset from said fixed axis, said method comprising:

activating the motorized flosser so that the flossing head oscillates arcuately about said fixed axis and said length of flossing material oscillates arcuately and simultaneously translates back and forth;

moving said flossing material vertically between adjacent teeth while the motorized flosser is so activated; and while moving said flossing material vertically between the adjacent teeth, simultaneously slightly pressing and pulling said flossing material gently toward and away from one of the adjacent teeth.

41. The method of claim 40 wherein the tines of the flossing head and the flossing material move arcuately through an arc of approximately 45 degrees during each oscillatory cycle of the flossing head.

42. The method of claim 40 wherein the tines of the flossing head and the flossing material move arcuately through an arc of between 30 and 75 degrees during each oscillating cycle of the flossing head.

43. The method of claim 40 wherein the flossing head oscillates at a frequency between 2,000 and 3,000 cycles per minute.

44. A method of flossing teeth with a motorized flosser having a flossing head including a pair of tines between which there extends a length of flossing material, said flossing head being arcuately oscillatable about a fixed axis, said method comprising:

activating the motorized flosser so that the flossing head oscillates arcuately about said fixed axis and said length of flossing material oscillates arcuately and simultaneously translates back and forth;

moving said flossing material vertically between adjacent teeth while the motorized flosser is so activated; and while moving said flossing material vertically between the adjacent teeth, simultaneously slightly pressing and pulling said flossing material gently toward and away from one of the adjacent teeth; and inserting toothpaste into a toothpaste holder secured to the flosser head prior to activating the motorized flosser such that the teeth are cleaned by the toothpaste and the flossing material while simultaneously being flossed and polished by the oscillating and translatory flossing material.

45. A method of removing plaque and biofilm from the surface of teeth comprising:

activating a motorized flosser having a flossing head so that the flosser head of the motorized flosser oscillates arcuately about a fixed axis;

pressing a length of flossing material extending between and secured to two tines of the flossing head vertically between adjacent teeth while the flossing head continues to oscillate arcuately and the length of flossing material oscillates arcuately, wherein said length of flossing material is offset from said fixed axis;

while the length of flossing material is pressed vertically between adjacent teeth and continues to oscillate, gently and repeatedly pressing the flossing material toward and away from one of the adjacent teeth.

46. A method of removing plague and biofilm from the surface of teeth comprising:
    activating a motorized flosser having a flossing head so that the flosser head of the motorized flosser oscillates arcuately about a fixed axis;
    pressing a length of flossing material extending between and secured to two tines of the flossing head vertically between adjacent teeth while the flossing head continues to oscillate arcuately and the length of flossing material oscillates arcuately;
    while the length of flossing material is pressed vertically between adjacent teeth and continues to oscillate, gently and repeatedly pressing the flossing material toward and away from one of the adjacent teeth; and
    placing toothpaste upon bristles mounted upon the flossing head before activating the motorized flosser.

47. A method of removing plague and biofilm from the surface of teeth comprising:
    activating a motorized flosser having a flossing head so that the flosser head of the motorized flosser oscillates arcuately about a fixed axis;
    pressing a length of flossing material extending between and secured to two tines of the flossing head vertically between adjacent teeth while the flossing head continues to oscillate arcuately and the length of flossing material oscillates arcuately;
    while the length of flossing material is pressed vertically between adjacent teeth and continues to oscillate, gently and repeatedly pressing the flossing material toward and away from one of the adjacent teeth; and
    placing toothpaste upon bristles secured to the tines of the flossing head before activating the motorized flosser so that the flosser is operative when activated to simultaneously brush the teeth with the bristles and to floss and polish the teeth with the flossing material.

* * * * *